(12) United States Patent
Stone et al.

(10) Patent No.: US 9,265,774 B2
(45) Date of Patent: Feb. 23, 2016

(54) METHODS, COMPOUNDS AND PHARMACEUTICAL COMPOSITIONS FOR TREATING ANXIETY AND MOOD DISORDERS

(75) Inventors: Eric A. Stone, Chappaqua, NY (US); Lin Yan, Jersey City, NJ (US); David Quartermain, New York, NY (US); Yasmeen Sarfraz, Jackson Heights, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/112,016

(22) PCT Filed: Apr. 13, 2012

(86) PCT No.: PCT/US2012/033485
§ 371 (c)(1),
(2), (4) Date: Dec. 30, 2013

(87) PCT Pub. No.: WO2012/142388
PCT Pub. Date: Oct. 18, 2012

(65) Prior Publication Data
US 2014/0107087 A1 Apr. 17, 2014

Related U.S. Application Data

(60) Provisional application No. 61/517,224, filed on Apr. 15, 2011.

(51) Int. Cl.

| | | |
|---|---|---|
| *A61K 31/573* | (2006.01) | |
| *A61K 31/24* | (2006.01) | |
| *A61K 31/35* | (2006.01) | |
| *A61K 31/13* | (2006.01) | |
| *A61K 31/137* | (2006.01) | |
| *A61K 31/138* | (2006.01) | |
| *A61K 45/06* | (2006.01) | |
| *A61K 31/135* | (2006.01) | |

(52) U.S. Cl.
CPC ............ *A61K 31/573* (2013.01); *A61K 31/13* (2013.01); *A61K 31/135* (2013.01); *A61K 31/137* (2013.01); *A61K 31/138* (2013.01); *A61K 31/24* (2013.01); *A61K 45/06* (2013.01)

(58) Field of Classification Search
None
See application file for complete search history.

(56) References Cited

U.S. PATENT DOCUMENTS 6,239,134 B1 * 5/2001 Sabb et al. ............... 514/253.1
2005/0171110 A1 8/2005 Yu et al.

OTHER PUBLICATIONS

Schmidt, et al., Behav Pharmacol., "The role of neurotrophic factors in adult hippocampal neurogenesis, antidepressant treatments and animal models of depressive-like behavior," 2007; 18(5-6): 391-418.
Simson, et al., Neuropharmacology, "Reversal of behavioral depression by infusion of an alpha-2 adrenergic agonist into the locus coeruleus," 1986; 25: 385-389.
Smadja, et al., Psychopharmacology (Berl), "CCK-B receptors in the limbic system modulate the antidepressant-like effects induced by endogenous enkephalins," 1997; 132(3): 227-36.
Smith, et al., Brain Struct Funct, "Noradrenergic transmission in the extended amygdala: role in increased drug-seeking and relapse during protracted drug abstinence," 2008; 213(1-2): 43-61.
Spear, et al., Eur J Pharmacol, "Low doses of the 5-HT1A receptor agonist 8-OH-DPAT increase ingestive behavior in late preweanling and postweanling, but not neonatal rat pups," 1991; 203(1): 9-15.
Steciuk, et al., Brain Res., "Decrease in stress-induced c-FOS-like immunoreactivity in the lateral septal nucleus of learned helpless rats," 1999; 822(1-2): 256-9.
Stone, et al., "Depressive behavior in mice due to immune stimulation is accompanied by reduced neural activity in brain regions involved in positively motivated behavior", Progress in Neuropsychopharmacology & Biological Psychiatry, 2007; 60: 803-811.
Stone, et al., "Open-Space Forced Swim Model of Unit 9.36 Depression for Mice", Current Protocols in Neuroscience, 2010; Supplement 54.
Stone, et al., "Gross mapping of alpha1-adrenoceptors that regulate behavioral activation in the mouse brain", Behav. Brain Res., 2004; 152: 167-175.
Stone, "Noradrenergic function during stress and depressions: An alternative view", Behavior & Brain Sciences, 1982; 5: 122.
Stone, "Problems with current catecholamine hypotheses of antidepressant agents: Speculations leading to a new hypothesis", Behavior & Brain Sciences, 1983; 6: 535-578.
Stone, et al., Brain Res, "Marked behavioral activation from inhibitory stimulation of locus coeruleus alpha1-adrenoceptors by a full agonist," 2009; 1291: 21-31.
Stone, et al., Int J Neuropsychopharmacol, "Antidepressant-like action of intracerebral 6-fluoronorepinephrine, a selective full alpha-adrenocepter agonist," 2011; 14(3): 319-31.
Stone, et al., Eur J Pharmacol., "Pharmacological blockade of brain alpha1-adrenoceptors as measured by ex vivo[3H] prazosin binding is correlated with behavioral immobility," 2001; 420(2-3): 97-102.
Stone, et al., Biol Psychiatry, "Drepressive behavior in mice due to immune stimulation is accompanied by reduced neural activity in brain regions involved in positively motivated behavior," 2006; 60(8): 803-11.
Stone, et al., Neurosci Biobehav Rev., "A final common pathway for depression? Progress toward a general conceptual framework," 2008a: 32(3): 508-24.
Stone, et al., Neuroscience, Brain alpha 1-adrenergic neurotransmission is necessary for behavioral activation to environmental change in mice, 1999; 94(4): 1245-52.
Stone, et al., Synapse, "Role of locus coeruleus alpha1-adrenoceptors in motor activity in rats," 2004; 54(3): 164-72.

(Continued)

*Primary Examiner* — Thomas S Heard
(74) *Attorney, Agent, or Firm* — Klauber & Jackson LLC

(57) ABSTRACT

Pharmaceutical compositions containing a cocktail of inhibitors of central stress nuclei are provided. The pharmaceutical compositions are useful for the prevention and treatment of a variety of conditions in mammals including humans, including anxiety and mood disorders such as depression.

3 Claims, 15 Drawing Sheets

(56) References Cited

OTHER PUBLICATIONS

Stone, et al., Behav Brain Res., Gross mapping of alpha1-adrenoceptors that regulate behavioral activation in the mouse brain, 2004; 152(2): 165-75.

Stout, et al., "Increased corticotropin-releasing factor concentrations in the bed nucleus of the stria terminalis of anhedonic rates", European Journal of Pharmacology, 2000; 401: 39-46.

Sun, et al., J Neurosci Methods, "Open space swimming test to index antidepressant activity," 2003; 126: 35-40.

Sun et al., Behav Pharmacol., "Effects of age on susceptibility to the induction of depressive behavior and imipramine in rats," 2008; 19(4): 334-8.

Surget, et al., Neuropsychopharmacology, "Corticolimbic transcriptome changes are state-depressant and region-specific in a rodent model of depression and of antidepressant reversal," 2009; 34(6): 1363-80.

Taylor, et al., Psychopharmacology (Berl), "Clonidine infusions into the locus coeruleus attenuate behavioral and neurochemical changes associated with naloxone-precipitated withdrawal," 1988; 96(1): 121-34.

Valentino, et al., Euro J Pharmacol., "Convergent regulation of locus coeruleus activity as an adaptive response to stress," 2008; 583(2-3): 194-203.

Weiss, et al., Neuropeptides, "Testing the hypothesis and locus coeruleus hyperactivity produces depression-related changes via galanin," 2005; 39: 281-287.

Weiss, et al., Neuropharmacology, "Infusion of adrenergic receptor agonists and antagoinists into the locus coeruleus and ventrical system of the brain, Effects on swim-motivated and spontaneous motor activity," 1986; 25(4): 367-84.

Yirmiya, Brain Res, "Endotoxin produces a depressive-like episode in rats," 1996; 711(1-2): 164-74.

Zarate, et al., Arch Gen Psychiatry, "A randomized trial of an N-methyl-D-asparate antagonist in treatment-resistant major depression," 2006; 61(8): 856-64.

Zhao, et al., Brain Res., "The varying effects of short-term and long-term corticosterone injections on depression-like behavior in mice", 2009; 1261: 83-90.

Zoumakis, et al., Ann NY Acad Sci., "Potentia use of corticotropin-releasing hormone antagoinists," 2006; 1083: 239-51.

Lopez, et al., Biological Psychiatry, "Role of Biological and Psychological Factors in Early Development and their Impact on Adult Life," 1999; 46: 1461-1471.

Stone, et al., Brain Research Reviews, "The role of the central noradrenergic system in behavioral inhibition," 2011; 3 (67): 193-208.

Adler, et al., J Pharmacol Exp Ther., "Receptor reserve at the alpha-2 adrenergic receptor in the rat cerebral cortex," 1987; 240(2): 508-15.

Arnsten, et al., Biol Psychiatry, "Neurobiology of executive functions: catecholamine influences on prefrontal cortical functions," 2005; 57(11): 1377-84.

Aston-Jones, et al., Annu Rev Neurosci., "An integrative theory of locus coeruleus-norepinephrine function: adaptive gain and optimal performance," 2005; 28: 403-50.

Bernal-Mizrachi, et al., Cell Metab, "An afferent vagal nerve pathway links hepatic PPARalpha activation to glucocorticoid-induced insulin resistance and hypertension," 2007; 5(2): 91-102.

Berridge, et al., Psychol Med, "Noradrenergic modulation of cognitive function: clinical implications of anatomical, electrophysiological and behavioural studies in animal models," 1993; 23(3): 557-64.

Bissette, et al., Neuropsychopharmacology, "Elevated concentrations of CRF in the locus coeruleus of depressed subjects," 2003; 28(7): 1328-35.

Blair-West, et al., Acta Psychiatr Scand, "Down-rating lifetime suicide risk in major depression," 1997; 95(3): 259-63.

Bouret, et al., Trends Neurosci, "Network reset: a simplified overarching theory of locus coeruleus noradrenaline function," 2005; 28(11): 574-82.

Brasili, et al., Eur J Pharmacol, "Fluoronorepinephrines: further pharmacological evaluation in vitro and in pithed rats," 1987; 144(2): 141-6.

Carr, et al., Neuropsychopharmacology, "Antidepressant-like effects of kappa-opioid receptor antagonists in Wistar Kyoto rats," 2010; 35(3): 752-64.

Cedarbaum, et al., J Comp Neurol, "Afferent projections to the rat locus coeruleus as determined by a retrograde tracing technique," 1978; 178(1): 1-16.

Dallman, et al., Ann NY Acad Sci., "Characterization of corticosterone feedback regulation of ACTH secretion," 1987; 512: 402-14.

Daly, et al., J Pharmacol Exp Ther, "Fluoronorepinephrines: specific agonists for the activation of alpha and beta adrenergic-sensitive cyclic AMP-generation systems in brain slices," 1980; 212(3): 382-9.

Drevets, et al., Eur Neuropsychopharmacol, "Functional anatomical correlates of antidepressant drug treatment assessed using PET measures of regional glucose metabolism," 2002; 12(6): 527-44.

Sartorius, et al., Int J Neuropsychopharmacol, "Antidepressant medications and other treatments of depressive disorders: A CINP Task Force report based on a review of evidence," 2007; 10 Suppl 1: S1-207.

Friedman, et al., Neuropsychopharmacology, "Programmed acute electrical stimulation of ventral tegmental area alleviates depressive-like behavior," 2009; 34(4): 1057-66.

Ghaisas, et al., J Ethnopharmacol, "Effect of Tectona grandis Linn. on dexamethasone-induced insulin resistance in mice," 2009; 122(2): 304-7.

Goodwin, et al., Biochem Biophys Res Commun, "The glucocorticoid receptor in the distal nephron is not necessary for the development or maintenance of dexamethasone-induced hypertension," 2010; 394(2): 266-71.

Gourley, et al., Bio Psychiatry, "Acute hippocampal brain-derived neurotrophic factor restores motivational and forced swim performance after corticosterone," 2008; 64(10): 884-90.

Grant, et al., Bio Psychiatry, "Effects of chronic antidepressant drug administration and electroconvulsive shock on locus coeruleus electrophysiologic activity," 2001; 49(2): 117-29.

Greenberg, et al., Biol Psychiatry, "Dexamethasone suppression test in helpless rats," 1989; 26(5): 530-2.

Hare, et al., Clin Pharmacol Ther, "Bioavailability of dexamethasone. II. Dexamethasone phosphate," 1975; 18(3): 330-7.

Hermann, et al., J Physiol, "Alpha-1 adrenergic input to solitary nucleus neurones: calcium oscillations, excitation and gastric reflex control," 2005; 562(Pt 2): 553-68.

Inskip, et al., Br J Psychiatry, "Lifetime risk of suicide for affective disorder, alcoholism and schizophrenia," 1998; 172: 35-7.

Introini-Collison, et al., "Memory-enhancing effects of post-training dipivefrin and epinephrine: involvement of peripheral and central adrenergic receptors", Ines Brain Res., 1977; 572: 81-86.

Johnson, et al., Eur J Pharmacol, "Characterization of alpha 1-adrenoceptors which increase cyclic AMP accumulation in rat cerebral cortex," 1986, 129(3): 293-305.

Jones, et al., J Comp Neurol, "Anatomy of brain alpha 1-adrenergic receptors: in vitro autoradiography with [125I]-heat," 1985; 231(2): 190-208.

Jurgens, et al., Mol Pharmacol, "Alpha2A adrenergic receptor activation inhibits epileptiform activity in the rat hippocampal CA3 region," 2007; 71(6): 1572-81.

Kasper, et al., World J Biol Psychiatry, "Beyond the monoaminergic hypothesis: agomelatine, a new antidepressant with innovative an innovative mechanism of action," 2009; 10(2): 117-26.

Keller-Wood, et al., Endo Rev., 1982; 5: 1-24.

Kort, et al., Neuropharmacology, "Increased turnover of norepinephrinie in the rat cerebral cortex during stress: role of the locus coeruleus," 1973; 12(10): 933-8.

Law-Tho, et al., Eur J Neurosci, "Noradrenaline decreases transmission of NMDA- and non-NMDA-receptor mediated monosynaptic EPSPs in rat prefrontal neurons in vitro," 1993; 5(11): 1494-500.

Lei, et al., J Neurophysiol, "Adrenergic facilitation of GABAergic transmission in rat entorhinal cortex," 2007; 98(5): 2868-77.

(56) References Cited

OTHER PUBLICATIONS

Lin, et al., Neuropsychopharmacology, "Role of alpha(1)-adrenoceptors of the locus coeruleus in self-stimulation of the medial forebrain bundle," 2007; 32(4): 835-41.

Lopez-Figueroa, et al., Biol Psychiatry, "Serotonin 5-HT1A, 5HT1B and 5HT2A receptor mRNA expression in subjects with major depression, bipolar disorder, and schizophrenia," 2004; 55(3): 225-33.

Lucas, et al., Neuron, "Serotonin(4) (5-HT(4)) receptor agonists are putative antidepressants with a rapid onset of action," 2007; 55(5): 712-25.

Ma, et al., Neuroscience, "Chronic intermittent hypoxia sensitizes acute hypothalmic-potuitary-adrenal stress reactivity and Fos induction in the rat locus coeruleus in response to subsequent immobilization stress," 2008; 154(4): 1639-47.

Machado-Vieira, et al., Pharmacol Ther, "Ketamine and the next generation of antidepressants with a rapid onset of action," 2009; 123(2): 143-50.

Maier, et al., Behav Neurosci, "8-OH-DPAT microinjected in the region of the dorsal raphe nucleus blocks and reverses the enhancement of fear conditioning and interference with escape produced by exposure to inescapable shock," 1995; 109(3): 404-12.

Malkesman, et al., Biol Psychiatry, "The female urine sniffing test: a novel approach for assessing reward-seeking behavior in rodents," 2010; 67(9): 864-71.

Mayberg, et al., Neuron, "Deep brain stimulation for treatment-resistant depression," 2005; 45(5): 651-60.

Mayberg, Biol Psychiatry, "Defining the neural circuitry of depression: toward a new nosology with therapeutic implications," 2007; 61(6): 729-30.

McElligott, et al., Neuropsychipharmacology, "Alpha1-adrenergic receptor-induced heterosynaptic long-term depression in the bed nucleus of the stria terminalis is disrupted in mouse models of affective disorders," 2008; 33(10): 2313-23.

Muigg, Biological Psychiatry, "Altered Brain Activation Pattern Associated With Drug-Induced Attenuation of Enhanced Depression-Like Behavior in Rats Bred for High Anxiety", 2007; 61: 783-796.

Nalivaiko, et al., Am J Pshysiol Regul Integr Comp Physiol, "Activation of 5-HT1A receptors in the medullary raphe reduces cardiovascular changes elicited by acute psychological and inflammataory stresses in rabbits," 2005; 289(2): R596-R604.

Nestler, et al., Biol Psychiatry, "Molecular control of locus coeruleus neurotransmission," 1999; 46(9): 1131-9.

Ordway, et al., Biol Psychiatry, "Elevated agonist binding to alpha2-adrenoceptors in the locus coeruleus in major depression," 2003; 53(4): 315-23.

Pertovaara, Prog Neurobil,"Noradrenergic pain modulation," 2006; 80(2): 52-83.

Price, et al., Neuropsychopharmacology, "Neurocircuitry of mood disorders," 2010; 35(1): 192-216.

\* cited by examiner

**LPS - Anhedonia:
Effect of dp6FNE on FUST**

METHODS, COMPOUNDS AND PHARMACEUTICAL COMPOSITIONS FOR TREATING ANXIETY AND MOOD DISORDERS

CROSS REFERENCE TO RELATED APPLICATIONS

This application is a National Stage of International Application No. PCT/US2012/033485, filed Apr. 13, 2012, which claims the benefit of priority to U.S. Provisional Application No. 61/517,224 filed Apr. 15, 2011. Applicants claim the benefit of 35 U.S.C. §120 as to the PCT application and priority under 35 U.S.C. §119 as to said United States provisional application, and the disclosures of both applications are expressly incorporated herein by reference in their entireties.

FIELD OF THE INVENTION

This invention relates to novel pharmaceutical compositions comprising a compound or a prodrug of a compound capable of modulating both $\alpha 1$- and $\alpha 2$-adrenergic receptor, two or more inhibitors of central stress nuclei, and a carrier. Specifically, the invention relates to novel pharmaceutical composition comprising a prodrug of a full agonist of $\alpha 1$- and $\alpha 2$-adrenergic receptor, a glucocorticoid receptor agonist, a serotonergic 5HT1A receptor agonist, an additional adrenergic agonist, and a carrier. This combination may be designed to produce rapid antidepressant action which is significantly faster than all currently available antidepressant drugs or agents. This invention also relates to methods for the prevention, prophylaxis and/or treatment of conditions that are causally related to depression, stress or other disorders. Specifically, the invention relates to methods for treating anxiety disorders or mood disorders using a cocktail of inhibitors of central stress nuclei.

BACKGROUND OF THE INVENTION

Major depressive illness represents one of the leading causes of disability with an estimated lifetime prevalence of 16.2% and an eventual suicide rate of from 6-15% (Blair-West, et al., *Acta Psychiatr.Scand.* (1997) 95:259-263; Inskip, et al., *Br. J. Psychiatry* (1998) 172:35-37) While numerous antidepressant drugs are currently available and are partially effective, most fail to produce remission in a significant fraction of patients. This lack of adequately efficacious antidepressants may be due to our present inadequate understanding of the underlying pathophysiology and neurobiology of major depression.

A number of new candidate drugs and procedures have been developed to overcome some of these difficulties. These include ketamine (Zarate, et al., *Arch Gen Psychiatry* 2006; 63: 856-864), 51-1T4 receptor agonists (Lucas, et al., *Neuron*, 2007; 55: 712-725), deep brain stimulation (Mayberg, et al., *Neuron* 2005; 45: 651-660, 2005), agomelatin (Kasper, et al., *World J Biol Psychiatry* 2009; 10: 117-126), and antagonists of CRF (Zoumakis, et al., *Ann N Y Acad Sci* 2006; 1083: 239-251), NK1 (Ebner, et al., *Curr Pharm Des* 2009; 15: 1647-1674), kappa opioid (Carr, et al., *Neuropsychopharmacology* 2010; 35: 752-763), and cholecystokinin (Smadja, et al., *Psychopharmacology* 1997; 132: 227-236) receptors. While some of these agents appear to have an increased speed of action and reduced side effect profile, they may not possess greater efficacy than existing drugs and may have further limitations themselves in terms of degree of invasiveness, losses of efficacy with chronic administration, and dissociative side effects. Moreover, while some of the newer agents can rapidly reverse the motoric (i.e., immobility) aspects of depression, most continue to have delayed actions on depressive anhedonia, one of the core symptoms of the illness (Friedman, et al., *Neuropsychopharmacology* 2009; 34: 1057-1066, Machado-Vieira, et al., *Pharmacol Ther* 2009; 123: 143-150).

Recently, however, the picture has begun to improve with significant advances in the elucidation of the basic neural circuitry of this disorder. In global terms, it now appears that depression arises from a shift of neural activity away from brain regions involved in motivation and behavioral performance towards regions involved in stress responses. (Mayberg, *Biological Psychiatry* 2007, 61: 729-730; Steciuk et al., *Brain Research*, 1999; 822: 256-259; Price et al., *Neuropsychopharmacology*, 2010, 35; 192-216 and Drevets, *European Neuropsychopharmacology*, 2009; 12:527-544; Stone et al., *Neuroscience and Biobehavioral Reviews*, 2008; 32:508-524). Thus, in both depressed patients and animal models of the disorder, brain structures controlling executive functions and behavioral performance such as the dorsolateral prefrontal motor and piriform cortex, lateral septal nucleus and nucleus accumbens tend to be deactivated or unresponsive to stimulation whereas areas controlling emotional and autonomic responses to stress including ventral limbic forebrain structures, amygdala, insula, bed nucleus of the stria terminalis, paraventricular nucleus of the hypothalamus and locus coeruleus tend to be overly activated or hyperresponsive.

The shift of activity between the motivational and stress regions has suggested that the heightened activity of the stress areas is the cause of the inhibition of the motivational regions.

Depression has a lifetime prevalence of approximately 17% with an economic burden of about $80 billion per year in our country. Currently available antidepressants are inadequate to meet this need because most have an unsatisfactory efficacy in a sizable fraction of patients and/or require several weeks to act, which can be especially deleterious for agitated, suicidal patients. It may, however, be possible to overcome these problems with the use of agents that immediately and selectively inhibit the brain's stress circuit via sensitive autoreceptors.

Various clinical neuroimaging and animal depression studies have shown that a key etiological factor in depression is the excessive activity of the central stress circuit, (Stone et al., 2008a) a group of brain nuclei that are highly sensitive to stress and that mediate the various autonomic, neuroendocrine, behavioral and aversive emotional responses to stressful stimuli. These findings therefore have suggested that it may be possible to initially treat depression rapidly and effectively by selectively targeting the central stress nuclei for acute inhibition, and that this method might help bridge the gap between the acute and chronic treatments of the illness.

Such a strategy was first employed by Weiss and colleagues (Simson et al., *Neuropharmacology* (1986) 25:385-389) and was directed at the locus coeruleus (LC), the main noradrenergic stress nucleus of the brain, which had been implicated in human depression (Bissette et al., *Neuropsychopharmacology* (2003) 28:1328-1335; Ordway et al., *Biol. Psychiatry* (2003) 53:315-323). Simson et al. studied rats who showed increased depressive-like immobility in a forced swim test as a result of previous exposure to traumatic electric shock stress. They found that infusion of the $\alpha_2$-adrenergic agonist, clonidine, in the LC to inhibit the latter's electrical activity, produced an immediate reduction of the depressive behavior consistent with the hypothesized role of the nucleus. Subsequently Stone et al provided further confirmatory evidence on the basis of experiments with another α-agonist, 6-fluoronorepinephrine, (6FNE), which produces an even more profound inhibition of the LC activity than clonidine as a result of the combined stimulation of inhibitory $\alpha_1$- and $\alpha_2$-receptors (Stone, et al., *International Journal of Neuropsychopharmacology* In press (2009); Stone, et al., *Brain Res.* (2009) 1291:21-31). This compound produced a more marked and rapid antidepressant response than clonidine when infused in the LC prior to several different behavioral tests. These findings have recently been confirmed by Stone et al in studies with dipivalyl-6-fluoronorepinephrine (dp6FNE), a catecholamine pro-drug that stimulates the 2 chief α-adrenergic inhibitory autoreceptors of the LC (Stone et al, *Current Protocols in Neuroscience* (2010) In press) This drug, at or below 1 mg/kg, i.p., h has been found to have immediate anti-immobility effects without motor stimulation or sedation in a model of chronic depression in mice (repeated forced swim) that is resistant to acute treatment with all other currently available antidepressants so far tested, including ketamine (FIG. 1) (Stone et al., *Current Protocols in Neuroscience* (2010) In press).

The mechanism by which excessive LC activity might lead to depression may involve the release of the inhibitory peptide galanin from noradrenergic fibers in the ventral tegmental area (Weiss, et al., *Neuropeptides* (2005) 39:281-287), thus inhibiting a key dopaminergic motivational behavioral system. Alternatively, it may involve excessive activation of postsynaptic $\alpha_1$-adrenoceptors by NE itself in certain forebrain regions, such as the prefrontal cortex, causing the neural activity in the latter structure to be markedly inhibited (Arnsten, et al., *Biol. Psychiatry* (2005) 57:1377-1384).

Central α1-adrenoceptors have long been known to play an essential role in behavioral activation under a variety of experimental conditions. Blockade of these receptors in a number of brain regions produces immobility in novel surroundings whereas stimulation may lead to behavioral activation in familiar environments (Stone et al., *Neuroscience* 1999; 94:1245-1252; Stone et al., *Neuropharmacology* 2001: 401: 354-261; Stone et al., *Behav. Brain Res.* 2004; 152:167-175). The LC appears to be a key region in this system in that it contains a dense concentration of al-receptor binding sites (Jones et al., *J. Comp. Neurol.*, 1985; 231:190-208; Stone et al., *Synapse*, 2004, 54; 164-172) having the above behavioral properties (Stone et al., *Behav. Brain Res.* 2004; 152:167-175; Stone et al., *Synapse*, 2004; 54:164-172; Lin et al., *Neuropsychopharmacology*, 2007; 32:835-841). Moreover this nucleus is a site of convergence for systems regulating arousal (Cedarbaum, et al., *J. Comp. Neurol.* 1978; 178:1-16; Berridge et al., *Psychol. Med.* 1993; 23:557-564), motivated behavior (Aston-Jones; et al., *Annu. Rev. Neurosci.* 2005; 28:403-450; Bouret, et al., *Trends Neurosci.* 2005; 28:574-582), stress (Valentino, et al., *Eur. J. Pharmacol.* 2008; 583: 194-203; Ma et al., *Neuroscience* 2008; 154:1639-1647; Korf et al., *Neuropharmacology* 1973, 12:933-938) and pain (Pertovaara, *Prog. Neurobiol.* 2006; 80:53-83) and can affect a wide range of behavioral and physiological functions.

While α1-adrenoceptors have traditionally been thought to mediate postsynaptic excitation (Hermann et al., *J. Physiol.* 2005; 562:553-568), several recent studies have shown that they can also depress excitatory synaptic or increase GABAergic neurotransmission in a number brain regions (McElligott, et al., *Neuropsychopharmacology* 2008; 33:2313-2323; Lei et al., *J. Neurophysiol.* 2007; 98:2868-2877). A reduced functional activity of the LC is known to lead to the activation of task-specific behaviors (Aston-Jones, et al., *Annu. Rev. Neurosci.* 2005; 28:403-450; Weiss et al., *Neuropharmacology* 1986; 25:367-384; Grant, et al., *Biol. Psychiatry* 2001; 49:117-129), while excessive LC activity has been shown to cause aversion and abandonment of rewarding behaviors (Smith et al., *Brain Struct. Funct* 2008, 213; 43-61; Taylor et al., *Psychopharmacology* 1988, 96; 121-134), and possibly depression (Grant et al., *Biol. Psychiatry* 2001, 49; 117-129; Simson et al., *Neuropharmacology* 1986; 25:385-389; Stone, *Behavior and Brain Sciences* 1982; 5:122). Determining how the functional activity of this nucleus is affected by α1-adrenergic stimulation that produces behavioral activation previously utilized local infusion of the selective α1-agonist, phenylephrine (PE), which produces a weak stimulation of exploratory behavior in rats (Stone et al., *Synapse*, 2004; 54:164-172). PE, however, is known to be only a partial agonist at brain α1-adrenoceptors (Johnson, et al., *Eur. J. Pharmacol.* 1986; 129:293-305; Law-Tho et al., *Eur. J. Neurosci* 1993; 5:1494-1500). In contrast, 6-fluoronorepinephrine (6FNE), which is the only known selective full agonist at all central α-adrenoceptors (Johnson et al., *Eur. J. Pharmacol.* 1986; 129; Brasili et al., *Eur. J. Pharmacol.* 1987; 144:141-146), produces extreme hyperactivity in the home cage when infused in the mouse LC.

Stimulation of $\alpha_1$-receptors of the locus coeruleus with the full agonist, 6FNE, produced a virtually complete cessation of the neural activity of this nucleus whereas blockade of these receptors with the $\alpha_1$-antagonist, terazosin, produced an excitation of virtually every neuron of the nucleus, as measured from the expression of c-Fos its cells (Stone, et al., *International Journal of Neuropsychopharmacology* In press (2009)). The activity of the LC was therefore shown to be reciprocally or inversely related to the level of ongoing motivated behavioral activity. Since depression is accompanied by an inhibition of many of these motivated behaviors and by a hyperactivity of the LC, it was reasoned that inhibition of the nucleus by the full agonist, 6FNE, would produce a potent antidepressant action. This was confirmed by tests of the effects of local infusion of 6FNE near the LC on 4 different tests of antidepressant activity: the acute forced swim, acute tail suspension, chronic open space forced swim and lipopolysaccharide induced anhedonia (Stone, et al., *Brain Res.* (2009) 1291: 21-31). From tests of anxiety in the open field and of the activity of stress-related brain regions after local infusion of 6FNE, these experiments also revealed that stimulation of these α-adrenergic receptors of the LC may act by inhibition of the organism's state of stress.

One of the drawbacks of current antidepressant agents is their slowness of action. Most presently available drugs require several weeks administration before they produce clinically significant antidepressant effects ((Sartorius et al., *International Journal of Neuropsychopharmacology* (2007) 10 Suppl 1: S1-207). This can be especially deleterious for agitated or suicidal patients who require immediate relief of symptoms and who may be resistant to psychotherapeutic or cognitive/behavioral-based interventions. It would be especially beneficial to address this problem with the use of drugs that selectively and rapidly inhibit central stress-sensitive brain areas known to be active during depression.

SUMMARY OF THE INVENTION

In a first aspect, the present invention provides compounds, and pharmaceutical compositions having potency, specificity and selectivity in the prevention, prophylaxis, and treatment of depression, including for instance, major depression and dysthymia, and other related conditions described herein.

Accordingly, the invention provides pharmaceutical compositions to treat an anxiety disorder or a mood disorder comprising an inhibitor of an α-adrenergic receptor and two or more inhibitors of central stress nuclei.

The invention further provides pharmaceutical compositions to treat an anxiety disorder or a mood disorder comprising:

a) a full agonist of α1- and α2-adrenoceptor;

b) a glucocorticoid receptor agonist;

c) a serotonergic 5HT1A receptor agonist; and d) a carrier or adjuvant.

The invention further provides pharmaceutical compositions to treat an anxiety disorder or a mood disorder comprising:

a) a prodrug of a full agonist of α1- and α2-adrenoceptor;

b) a glucocorticoid receptor agonist;

c) a serotonergic 5HT1A receptor agonist; and d) a carrier or adjuvant.

The invention further provides pharmaceutical compositions to treat an anxiety disorder or a mood disorder comprising:

a) a full agonist or a prodrug of a full agonist of α1- and α2-adrenoceptor;

b) a glucocorticoid receptor agonist;

c) a serotonergic 5HT1A receptor agonist;

d) an additional α-adrenergic modulator; and e) a carrier or adjuvant.

In one particular embodiment, with respect to the pharmaceutical composition, the full agonist of α1- and α2-adrenoceptor is according to formula I:

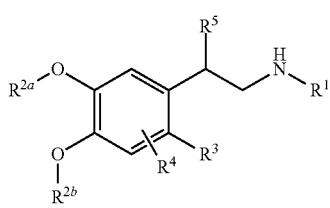

wherein $R^1$ is selected from H, and substituted or unsubstituted $C_1$-$C_6$ alkyl;

each $R^{2a}$, and $R^{2b}$ is independently selected from H, and an enzymatically cleavable group; provided that at least one of $R^{2a}$, and $R^{2b}$ is other than H;

each $R^3$ and $R^4$ is independently selected from H, halo, substituted or unsubstituted $C_1$-$C_6$ alkyl, substituted or unsubstituted halo $C_1$-$C_6$ alkyl, hydroxy, amino, and $C_1$-$C_6$ alkoxy;

$R^5$ is H, or OH;

or a pharmaceutically acceptable salt, or solvate thereof; and stereoisomers, isotopic variants and tautomers thereof.

In one particular embodiment, with respect to the pharmaceutical composition, the full agonist of α1- and α2-adrenoceptor is according to formula IIIc:

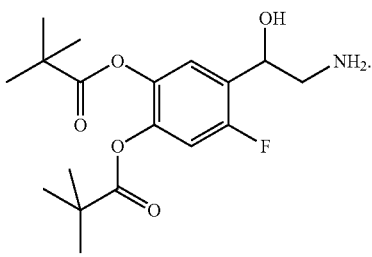

In one particular embodiment, with respect to the pharmaceutical composition, the 5HT1A receptor agonist is 8-OHD-PAT or 8-hydroxy-N,N-dipropyl-2-aminotetralin.

In one particular embodiment, with respect to the pharmaceutical composition, the glucocorticoid receptor agonist is corticosterone.

In another aspect, pharmaceutical compositions are provided comprising a compound of the invention, and a pharmaceutical carrier, excipient or diluent. The pharmaceutical composition can comprise one or more of the compounds described herein. In a further embodiment, the pharmaceutical compositions of the invention can comprise a compound in combination with one or more other compounds and/or compositions having a like therapeutic effect.

It will be understood that compounds of the present invention useful in the pharmaceutical compositions and treatment methods disclosed herein, can be pharmaceutically acceptable as prepared and used.

In a second aspect, the present invention provides methods for preventing, treating or ameliorating an anxiety disorder or a mood disorder such as depression, including for instance major depression or dysthymia, by administering to a mammal in need thereof a therapeutically effective amount of one or more of the compounds provided herein or a pharmaceutical composition containing one or more of the compounds provided herein. The methods may be effective to prevent, treat or ameliorate the anxiety or mood disorder or reduce symptoms of anxiety or depression.

In some instances, the methods are effective to reduce the neural response in a stress response, particularly in regions of the brain active in a stress response such as, for instance the nucleus locus coeruleus or the paraventricular hypothalamus. Also, in some instances, the methods are effective to increase neural activity in areas of the brain involved in motivated behavior, such as, for instance, the nucleus accumbens or lateral septal nucleus. The methods may be effective to reduce the suppressing effects of stress on motivated behavior. In many instances, the compounds and compositions of the present invention are effective as agonists to α adrenoceptors, such as, for instance either or both of α1 and α2 adrenoceptors, preferably α1 receptor agonists. Likewise, the compounds and compositions of the present invention may be effective as agonists to either or both of α1A and α1B adrenoceptors, preferably α1B receptor agonists.

The methods may feature providing the compounds and compositions of the present invention by any effective means of delivery, such as, for instance orally or intravenously. The methods may provide an observable reduction in symptoms associated with an anxiety or mood disorder, such as depression or dysthymia, within a shorter time than provided by other therapies for an observable reduction in symptoms associated with an anxiety or mood disorder, such as depression or dysthymia. A reduction in one or more symptoms associated with an anxiety or mood disorder, such as depression or dysthymia, may be observable within 5 minutes, 15 minutes, 30 minutes, 1 hour, 2 hours, 6 hours, 12 hours, 1 day, 2 days, 3 days, 5 days, one week, 10 days, 2 weeks, 3 weeks, 1 month, 6 weeks, 2 months or 3 months. A reduction in one or more symptoms associated with an anxiety or mood disorder, such as depression or dysthymia, may be observable within at time period that is 10%, 20%, 25%, 30%, 40, 50%, 60%, 70%, 75%, 99.5% or more shorter than the time required for an observable reduction in one or more symptoms associated with an anxiety or mood disorder, such as depression or dysthymia provided by other therapies. The compounds and compositions of the present invention may be provided alone or in combination with one or more therapies, including one or more standard therapies for depression, such as, for instance, one or more tricyclic antidepressants, one or more serotonin reuptake inhibitors, or one or more monoamine oxidase inhibitors.

In addition to the methods of treatment, the present invention extends to the use of any of the compounds or compositions described herein for the preparation of medicaments that may be administered for such treatments, as well as to such compounds for the treatments disclosed and specified.

Accordingly, it is a principal object of the invention to provide pharmaceutical compositions effective to treat certain anxiety or mood disorders including, for instance, depression and dysthymia. A still further object of the invention is to provide a method for reducing symptoms associated with an anxiety or mood disorder such as depression or dysthymia. Other objects and advantages will become apparent to those skilled in the art from a consideration of the ensuing detailed description.

DETAILED DESCRIPTION OF THE INVENTION

Definitions

Figure 1:
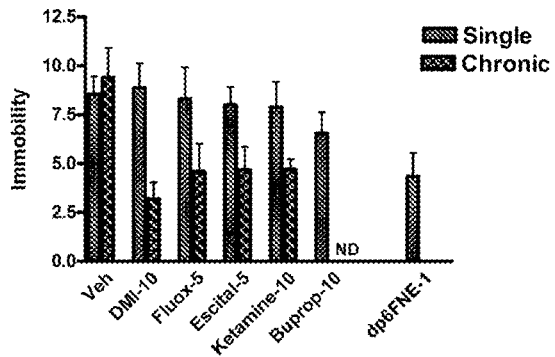
FIG. 1 provides a comparison of acute effect of i.p. dp6FNE with acute and chronic effects of currently available antidepressants on RFS test (dosages on abscissa). Chronic antidepressants administered by osmotic minipump for 14 d (N=3).

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Acyl' or 'Alkanoyl' refers to a radical —C(O)R$^{20}$, where R$^{20}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—$(CH_2)_t(C_6$-$C_{10}$ aryl), —C(O)—$(CH_2)_t$(5-10 membered heteroaryl), —C(O)—$(CH_2)_t(C_3$-$C_{10}$ cycloalkyl), and —C(O)—$(CH_2)_t$(4-10 membered heterocycloalkyl), wherein t is an integer from 0 to 4.

'Substituted Acyl' or 'Substituted Alkanoyl' refers to a radical —C(O)$R^{21}$, wherein $R^{21}$ is independently
$C_1$-$C_8$ alkyl, substituted with halo or hydroxy; or
$C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Acylamino' refers to a radical —$NR^{22}C(O)R^{23}$, where $R^{22}$ is hydrogen, $C_1$-$C_8$ alkyl, $C_3$-$C_{10}$ cycloalkyl, 4-10 membered heterocycloalkyl, $C_6$-$C_{10}$ aryl, arylalkyl, 5-10 membered heteroaryl or heteroarylalkyl and $R^{23}$ is hydrogen, $C_1$-$C_4$ alkyl, $C_3$-$C_{10}$ cycloalkyl, 4-10 membered heterocycloalkyl, $C_6$-$C_{10}$ aryl, arylalkyl, 5-10 membered heteroaryl or heteroarylalkyl, as defined herein. Exemplary 'acylamino' include, but are not limited to, formylamino, acetylamino, cyclohexylcarbonylamino, cyclohexylmethyl-carbonylamino, benzoylamino and benzylcarbonylamino. Particular exemplary 'acylamino' groups are —$NR^{24}C(O)$—$C_1$-$C_8$ alkyl, —$NR^{24}C(O)$—$(CH_2)_t(C_6$-$C_{10}$ aryl), —$NR^{24}C(O)$—$(CH_2)_t$(5-10 membered heteroaryl), —$NR^{24}C(O)$—$(CH_2)_t$($C_3$-$C_{10}$ cycloalkyl), and —$NR^{24}C(O)$—$(CH_2)_t$(4-10 membered heterocycloalkyl), wherein t is an integer from 0 to 4, and each $R^{24}$ independently represents H or $C_1$-$C_8$ alkyl.

'Substituted Acylamino' refers to a radical —$NR^{25}C(O)R^{26}$, wherein:
$R^{25}$ is independently
H, $C_1$-$C_8$ alkyl, substituted with halo or hydroxy; or
$C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and
$R^{26}$ is independently
H, $C_1$-$C_8$ alkyl, substituted with halo or hydroxy; or
$C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_4$ haloalkyl, unsubstituted $C_1$-$C_4$ hydroxyalkyl, or unsubstituted $C_1$-$C_4$ haloalkoxy or hydroxyl;
provided at least one of $R^{25}$ and $R^{26}$ is other than H.

'Acyloxy' refers to a radical —OC(O)$R^{27}$, where $R^{27}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—$(CH_2)_t(C_6$-$C_{10}$ aryl), —C(O)—$(CH_2)_t$(5-10 membered heteroaryl), —C(O)—$(CH_2)_t(C_3$-$C_{10}$ cycloalkyl), and —C(O)—$(CH_2)_t$(4-10 membered heterocycloalkyl), wherein t is an integer from 0 to 4.

'Substituted Acyloxy' refers to a radical —OC(O)$R^{28}$, wherein $R^{28}$ is independently
$C_1$-$C_8$ alkyl, substituted with halo or hydroxy; or
$C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkoxy' refers to the group —O$R^{29}$ where $R^{29}$ is $C_1$-$C_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocycloalkyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups are —O—$(CH_2)_t(C_6$-$C_{10}$ aryl), —O—$(CH_2)_t$(5-10 membered heteroaryl), —O—$(CH_2)_t(C_3$-$C_{10}$ cycloalkyl), and —O—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are OCF$_3$, OCH$_2$CF$_3$, OCH$_2$Ph, OCH$_2$-cyclopropyl, OCH$_2$CH$_2$OH, and OCH$_2$CH$_2$NMe$_2$.

'Alkoxycarbonyl' refers to a radical —C(O)—O$R^{30}$ where $R^{30}$ represents an $C_1$-$C_8$ alkyl, $C_3$-$C_{10}$ cycloalkyl, $C_3$-$C_{10}$ cycloalkylalkyl, 4-10 membered heterocycloalkylalkyl, aralkyl, or 5-10 membered heteroarylalkyl as defined herein. Exemplary "alkoxycarbonyl" groups are C(O)O—$C_1$-$C_8$ alkyl, —C(O)O—$(CH_2)_t(C_6$-$C_{10}$ aryl), —C(O)O—$(CH_2)_t$(5-10 membered heteroaryl), —C(O)O—$(CH_2)_t(C_3$-$C_{10}$ cycloalkyl), and —C(O)O—$(CH_2)_t$(4-10 membered heterocycloalkyl), wherein t is an integer from 1 to 4.

'Substituted Alkoxycarbonyl' refers to a radical —C(O)—O$R^{31}$ where $R^{31}$ represents:
$C_1$-$C_8$ alkyl, $C_3$-$C_{10}$ cycloalkyl, $C_3$-$C_{10}$ cycloalkylalkyl, or 4-10 membered heterocycloalkylalkyl, each of which is substituted with halo, substituted or unsubstituted amino, or hydroxy; or
$C_6$-$C_{10}$ aralkyl, or 5-10 membered heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Aryloxycarbonyl' refers to a radical —C(O)—O$R^{32}$ where $R^{32}$ represents an $C_6$-$C_{10}$ aryl, as defined herein. Exemplary "aryloxycarbonyl" groups is —C(O)O—$(C_6$-$C_{10}$ aryl).

'Substituted Aryloxycarbonyl' refers to a radical —C(O)—O$R^{33}$ where $R^{33}$ represents —$C_6$-$C_{10}$ aryl, substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Heteroaryloxycarbonyl' refers to a radical —C(O)—OR$^{34}$ where R$^{34}$ represents a 5-10 membered heteroaryl, as defined herein. An exemplary "aryloxycarbonyl" group is —C(O)O-(5-10 membered heteroaryl).

'Substituted Heteroaryloxycarbonyl' refers to a radical —C(O)—OR$^{35}$ where R$^{35}$ represents:

5-10 membered heteroaryl, substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Alkoxycarbonylamino' refers to the group —NR$^{36}$C(O)OR$^{37}$, where R$^{36}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein, and R$^{37}$ is $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)R$^{20}$), alkoxy, alkoxycarbonyl, alkoxycarbonylamino (—NR"-alkoxycarbonyl or —NH—C(O)—OR$^{27}$), amino, substituted amino, aminocarbonyl (carbamoyl or amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, aryloxy, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$-aryl. In a particular embodiment 'substituted alkyl' refers to a $C_1$-$C_8$ alkyl group substituted with halo, cyano, nitro, trifluoromethyl, trifluoromethoxy, azido, —NR'''SO$_2$R''', —SO$_2$NR''R''', —C(O)R''', —C(O)OR''', —OC(O)R''', —NR'''C(O)R''', —C(O)NR''R''', —NR''R''', or —(CR'''R'''')$_m$OR'''; wherein each R'' is independently selected from H, $C_1$-$C_8$ alkyl, —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), and —(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted haloalkoxy or hydroxy. Each of R''' and R'''' independently represents H or $C_1$-$C_8$ alkyl.

'Alkylene' refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

'Substituted alkylene' refers to those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkenyl' refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

'Substituted alkenyl' refers to those groups recited in the definition of 'substituted' herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkenylene' refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

'Alkynyl' refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

'Substituted alkynyl' refers to those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, aryloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Amino' refers to the radical —NH$_2$.

'Substituted amino' refers to an amino group substituted with one or more of those groups recited in the definition of 'substituted' herein, and particularly refers to the group —N($R^{38}$)$_2$ where each $R^{38}$ is independently selected from:

hydrogen, $C_1$-$C_8$ alkyl, $C_6$-$C_{10}$ aryl, 5-10 membered heteroaryl, 4-10 membered heterocycloalkyl, or $C_3$-$C_{10}$ cycloalkyl; or $C_1$-$C_8$ alkyl, substituted with halo or hydroxy; or —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl) or —(CH$_2$)$_t$(4-10 membered heterocycloalkyl) wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

When both $R^{38}$ groups are hydrogen, —N($R^{38}$)$_2$ is an amino group. Exemplary 'substituted amino' groups are —NR$^{39}$—$C_1$-$C_8$ alkyl, —NR$^{39}$—(CH$_2$)$_t$($C_6$-$C_{10}$ aryl), —NR$^{39}$—(CH$_2$)$_t$(5-10 membered heteroaryl), —NR$^{39}$—(CH$_2$)$_t$($C_3$-$C_{10}$ cycloalkyl), and —NR$^{39}$—(CH$_2$)$_t$(4-10 membered heterocycloalkyl), wherein t is an integer from 0 to 4, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term "substituted amino" includes the groups alkylamino, substituted alkylamino, alkylarylamino, substituted alkylarylamino, arylamino, substituted arylamino, dialkylamino and substituted dialkylamino as defined below.

'Alkylamino' refers to the group —NHR$^{40}$, wherein $R^{40}$ is $C_1$-$C_8$ alkyl;

'Substituted Alkylamino' refers to the group —NHR$^{41}$, wherein $R^{41}$ is $C_1$-$C_8$ alkyl; and the alkyl group is substituted with halo, substituted or unsubstituted amino, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkylarylamino' refers to the group —NR$^{42}$R$^{43}$, wherein $R^{42}$ is aryl and $R^{43}$ is $C_1$-$C_8$ alkyl.

'Substituted Alkylarylamino' refers to the group —NR$^{44}$R$^{45}$, wherein $R^{44}$ is aryl and $R^{45}$ is $C_1$-$C_8$ alkyl; and the alkyl group is substituted with halo, substituted or unsubstituted amino, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Arylamino' means a radical —NHR$^{46}$ where $R^1$ is selected from $C_6$-$C_{10}$ aryl and 5-10 membered heteroaryl as defined herein.

'Substituted Arylamino' refers to the group —NHR$^{47}$, wherein $R^{47}$ is independently selected from $C_6$-$C_{10}$ aryl and 5-10 membered heteroaryl; and any aryl or heteroaryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Dialkylamino' refers to the group —NR$^{48}$R$^{49}$, wherein each of $R^{48}$ and $R^{49}$ are independently selected from $C_1$-$C_8$ alkyl.

'Substituted Dialkylamino' refers to the group —NR$^{50}$R$^{51}$, wherein each of $R^{59}$ and $R^{51}$ are independently selected from $C_1$-$C_8$ alkyl; and at least one of the alkyl groups is independently substituted with halo, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Diarylamino' refers to the group —NR$^{52}$R$^{53}$, wherein each of $R^{52}$ and $R^{53}$ are independently selected from $C_6$-$C_{10}$ aryl.

'Aminosulfonyl' or 'Sulfonamide' refers to the radical —S(O$_2$)NH$_2$.

'Substituted aminosulfonyl' or 'substituted sulfonamide' refers to a radical such as —S(O$_2$)N(R$^{54}$)$_2$ wherein each $R^{548}$ is independently selected from:

H, $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{54}$ is other than H.

Exemplary 'substituted aminosulfonyl' or 'substituted sulfonamide' groups are —S(O$_2$)N(R$^{55}$)—$C_1$-$C_8$ alkyl, —S(O$_2$)N(R$^{55}$)—(CH$_2$)$_t$($C_6$-$C_{10}$ aryl), —S(O$_2$)N(R$^{55}$)—(CH$_2$)$_t$(5-10 membered heteroaryl), —S(O$_2$)N(R$^{55}$)—(CH$_2$)$_t$($C_3$-$C_{10}$ cycloalkyl), and —S(O$_2$)N(R$^{55}$)—(CH$_2$)$_t$(4-10 membered heterocycloalkyl), wherein t is an integer from 0 to 4; each $R^{55}$ independently represents H or $C_1$-$C_8$ alkyl; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted Aralkyl' or 'substituted arylalkyl' refers to an alkyl group, as defined above, substituted with one or more aryl groups; and at least one of the aryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

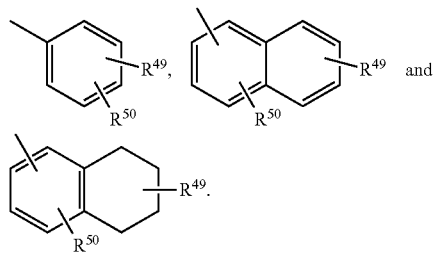

In these formulae one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocycloalkyl, alkanoyl, $C_1$-$C_8$ alkoxy, heteroaryloxy, alkylamino, arylamino, heteroarylamino, $NR^{58}COR^{59}$, $NR^{58}SOR^{59}$, $NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O or S. $R^{60}$, and $R^{61}$ are independently hydrogen, $C_1$-$C_8$ alkyl, $C_1$-$C_4$ haloalkyl, $C_3$-$C_{10}$ cycloalkyl, 4-10 membered heterocycloalkyl, $C_6$-$C_{10}$ aryl, substituted aryl, 5-10 membered heteroaryl.

'Fused Aryl' refers to an aryl having two of its ring carbon in common with a second aryl ring or with an aliphatic ring.

'Arylalkyloxy' refers to an —O-alkylaryl radical where alkylaryl is as defined herein.

'Substituted Arylalkyloxy' refers to an —O-alkylaryl radical where alkylaryl is as defined herein; and any aryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Azido' refers to the radical —$N_3$.

'Carbamoyl or amido' refers to the radical —$C(O)NH_2$.

'Substituted Carbamoyl' or 'substituted amido' refers to the radical —$C(O)N(R^{62})_2$ wherein each $R^{62}$ is independently
H, $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroarylalkyl; or
$C_1$-$C_8$ alkyl substituted with halo or hydroxy; or
$C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{62}$ is other than H.

Exemplary 'Substituted Carbamoyl' groups are —$C(O)NR^{64}$—$C_1$-$C_8$ alkyl, —$C(O)NR^{64}$—$(CH_2)_t(C_6$-$C_{10}$ aryl), —$C(O)N^{64}$—$(CH_2)_t$(5-10 membered heteroaryl), —$C(O)NR^{64}$—$(CH_2)_t(C_3$-$C_{10}$ cycloalkyl), and —$C(O)NR^{64}$—$(CH_2)_t$(4-10 membered heterocycloalkyl), wherein t is an integer from 0 to 4, each $R^{64}$ independently represents H or $C_1$-$C_4$ alkyl and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. 'Carboxy' refers to the radical —$C(O)OH$.

'Cycloalkyl' refers to cyclic non-aromatic hydrocarbyl groups having from 3 to 10 carbon atoms. Such cycloalkyl groups include, by way of example, single ring structures such as cyclopropyl, cyclobutyl, cyclopentyl, and cyclooctyl.

'Substituted cycloalkyl' refers to a cycloalkyl group as defined above substituted with one or more of those groups recited in the definition of 'substituted' herein, and particularly refers to a cycloalkyl group having 1 or more substituents, for instance from 1 to 5 substituents, and particularly from 1 to 3 substituents, in particular 1 substituent.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, e.g. cycloheteroalkenyl, and the like having from 1 to 5, and particularly from 1 to 3 heteroatoms.

'Heteroaryl' means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

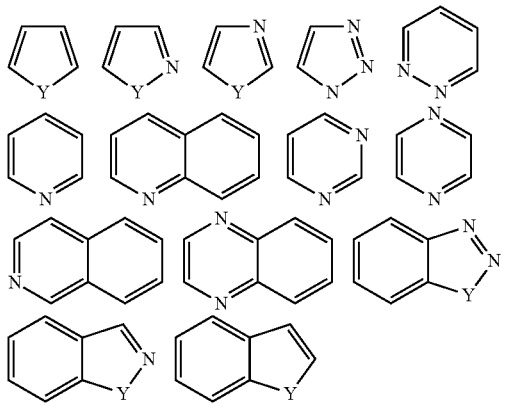

wherein each Y is selected from carbonyl, N, $NR^{65}$, O and S; and $R^{65}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

Examples of representative aryl having hetero atoms containing substitution include the following:

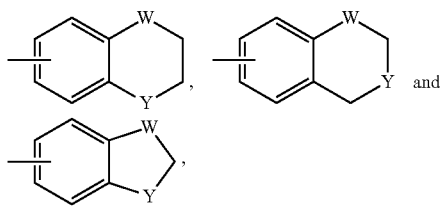

wherein each W is selected from $C(R^{66})_2$, $NR^{66}$, O and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

As used herein, the term 'heterocycloalkyl' refers to a 4-10 membered, stable heterocyclic non-aromatic ring and/or including rings containing one or more heteroatoms independently selected from N, O and S, fused thereto. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

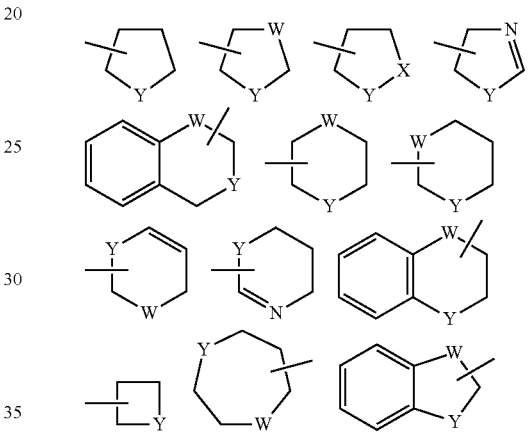

wherein each W is selected from $CR^{67}$, $C(R^{67})_2$, $NR^{67}$, O and S; and each Y is selected from $NR^{67}$, O and S; and $R^{67}$ is independently hydrogen, $C_1$-$C_8$ alkyl, $C_3$-$C_{10}$ cycloalkyl, 4-10 membered heterocycloalkyl, $C_6$-$C_{10}$ aryl, 5-10 membered heteroaryl, These heterocycloalkyl rings may be optionally substituted with one or more groups selected from the group consisting of acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

'Hydroxy' refers to the radical —OH.

'Nitro' refers to the radical —NO$_2$.

'Substituted' refers to a group in which one or more hydrogen atoms are each independently replaced with the same or different substituent(s). Typical substituents may be selected from the group consisting of:

halogen, —$R^{68}$, —O$^-$, =O, —OR$^{68}$, —SR$^{68}$, —S$^-$, =S, —NR$^{68}$R$^{69}$, =NR$^{68}$, —CCl$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{68}$, —OS(O$_2$)O$^-$, —OS(O)$_2$R$^{68}$, —P(O)(O$^-$)$_2$, —P(O)(OR$^{68}$)(O$^-$), —OP(O)(OR$^{68}$)(OR$^{69}$), —C(O)R$^{68}$, —C(S)R$^{68}$, —C(O)OR$^{68}$, —C(O)NR$^{68}$R$^{69}$, —C(O)O$^-$, —C(S) OR$^{68}$, —NR$^{70}$C(O)NR$^{68}$R$^{69}$, —NR$^{70}$C(S)NR$^{68}$R$^{69}$, —NR$^{71}$C)(NR$^{70}$)NR$^{68}$R$^{69}$ and —C(NR$^{70}$) NR$^{68}$R$^{69}$;

wherein each $R^{68}$, $R^{69}$, $R^{70}$ and $R^{71}$ are independently:
hydrogen, $C_1$-$C_8$ alkyl, $C_6$-$C_{10}$ aryl, arylalkyl, $C_3$-$C_{10}$ cycloalkyl, 4-10 membered heterocycloalkyl, 5-10 membered heteroaryl, heteroarylalkyl; or
$C_1$-$C_8$ alkyl substituted with halo or hydroxy; or
$C_6$-$C_{10}$ aryl, 5-10 membered heteroaryl, $C_6$-$C_{10}$ cycloalkyl or 4-10 membered heterocycloalkyl each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

In a particular embodiment, substituted groups are substituted with one or more substituents, particularly with 1 to 3 substituents, in particular with one substituent group.

In a further particular embodiment the substituent group or groups are selected from halo, cyano, nitro, trifluoromethyl, trifluoromethoxy, azido, —$NR^{72}SO_2R^{73}$, —$SO_2NR^{73}R^{72}$, —$C(O)R^{73}$, —$C(O)OR^{73}$, —$OC(O)R^{73}$, —$NR^{72}C(O)R^{73}$, —$C(O)NR^{73}R^{72}$, —$NR^{73}R^{72}$, —$(CR^{72}R^{72})_m OR^{72}$, wherein, each $R^{73}$ is independently selected from H, $C_1$-$C_8$ alkyl, —$(CH_2)_t(C_6$-$C_{10}$ aryl), —$(CH_2)_t$(5-10 membered heteroaryl), —$(CH_2)_t(C_3$-$C_{10}$ cycloalkyl), and —$(CH_2)_t$(4-10 membered heterocycloalkyl), wherein t is an integer from 0 to 4; and
any alkyl groups present, may themselves be substituted by halo or hydroxy; and
any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Each R" independently represents H or $C_1$-$C_6$alkyl.

'Substituted sulfanyl' refers to the group —$SR^{74}$, wherein $R^{74}$ is selected from:
$C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
$C_1$-$C_8$ alkyl substituted with halo, substituted or unsubstituted amino, or hydroxy; or
$C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'substituted sulfanyl' groups are —S—($C_1$-$C_8$ alkyl) and —S—($C_3$-$C_{10}$ cycloalkyl), —S—$(CH_2)_t(C_6$-$C_{10}$ aryl), —S—$(CH_2)_t$(5-10 membered heteroaryl), —S—$(CH_2)_t(C_3$-$C_{10}$ cycloalkyl), and —S—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. The term 'substituted sulfanyl' includes the groups 'alkylsulfanyl' or 'alkylthio', 'substituted alkylthio' or 'substituted alkylsulfanyl', 'cycloalkylsulfanyl' or 'cycloalkylthio', 'substituted cycloalkylsulfanyl' or 'substituted cycloalkylthio', 'arylsulfanyl' or 'arylthio' and 'heteroarylsulfanyl' or 'heteroarylthio' as defined below.

'Alkylthio' or 'Alkylsulfanyl' refers to a radical —$SR^{75}$ where $R^{75}$ is a $C_1$-$C_8$ alkyl or group as defined herein. Representative examples include, but are not limited to, methylthio, ethylthio, propylthio and butylthio.

'Substituted Alkylthio' or 'substituted alkylsulfanyl' refers to the group —$SR^{76}$ where $R^{76}$ is a $C_1$-$C_8$ alkyl, substituted with halo, substituted or unsubstituted amino, or hydroxy.

'Cycloalkylthio' or 'Cycloalkylsulfanyl' refers to a radical —$SR^{77}$ where $R^{77}$ is a $C_3$-$C_{10}$ cycloalkyl or group as defined herein. Representative examples include, but are not limited to, cyclopropylthio, cyclohexylthio, and cyclopentylthio.

'Substituted cycloalkylthio' or 'substituted cycloalkylsulfanyl' refers to the group —$SR^{78}$ where $R^{78}$ is a $C_3$-$C_{10}$ cycloalkyl, substituted with halo, substituted or unsubstituted amino, or hydroxy.

'Arylthio' or 'Arylsulfanyl' refers to a radical —$SR^{79}$ where $R^{79}$ is a $C_6$-$C_{10}$ aryl group as defined herein.

'Heteroarylthio' or 'Heteroarylsulfanyl' refers to a radical —$SR^{80}$ where $R^{80}$ is a 5-10 membered heteroaryl group as defined herein.

'Substituted sulfinyl' refers to the group —$S(O)R^{81}$, wherein $R^{81}$ is selected from:
$C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
$C_1$-$C_8$ alkyl substituted with halo, substituted or unsubstituted amino, or hydroxy; or
$C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'substituted sulfinyl' groups are —$S(O)$—($C_1$-$C_5$ alkyl) and —$S(O)$—($C_3$-$C_{10}$ cycloalkyl), —$S(O)$—$(CH_2)_t(C_6$-$C_{10}$ aryl), —$S(O)$—$(CH_2)_t$(5-10 membered heteroaryl), —$S(O)$—$(CH_2)_t(C_3$-$C_{10}$ cycloalkyl), and —$S(O)$—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. The term substituted sulfinyl includes the groups 'alkylsulfinyl', 'substituted alkylsulfinyl', 'cycloalkylsulfinyl', 'substituted cycloalkylsulfinyl', 'arylsulfinyl' and 'heteroarylsulfinyl' as defined herein.

'Alkylsulfinyl' refers to a radical —$S(O)R^{82}$ where $R^{82}$ is a $C_1$-$C_8$ alkyl group as defined herein. Representative examples include, but are not limited to, methylsulfinyl, ethylsulfinyl, propylsulfinyl and butylsulfinyl.

'Substituted Alkylsulfinyl' refers to a radical —$S(O)R^{83}$ where $R^{83}$ is a $C_1$-$C_8$ alkyl group as defined herein, substituted with halo, substituted or unsubstituted amino, or hydroxy.

'Cycloalkylsulfinyl' refers to a radical —$S(O)R^{84}$ where $R^{84}$ is a $C_3$-$C_{10}$ cycloalkyl or group as defined herein. Representative examples include, but are not limited to, cyclopropylsulfinyl, cyclohexylsulfinyl, and cyclopentylsulfinyl. Exemplary 'cycloalkylsulfinyl' groups are $S(O)$—$C_3$-$C_{10}$ cycloalkyl.

'Substituted cycloalkylsulfinyl' refers to the group —$S(O)R^{85}$ where $R^{85}$ is a $C_3$-$C_{10}$ cycloalkyl, substituted with halo, substituted or unsubstituted amino, or hydroxy.

'Arylsulfinyl' refers to a radical —$S(O)R^{86}$ where $R^{86}$ is a $C_6$-$C_{10}$ aryl group as defined herein.

'Heteroarylsulfinyl' refers to a radical —$S(O)R^{87}$ where $R^{87}$ is a 5-10 membered heteroaryl group as defined herein.

'Substituted sulfonyl' refers to the group —$S(O)_2R^{88}$, wherein $R^{88}$ is selected from:

$C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or $C_1$-$C_8$ alkyl substituted with halo, substituted or unsubstituted amino, or hydroxy; or $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'substituted sulfonyl' groups are —S(O)$_2$—($C_1$-$C_8$ alkyl) and —S(O)$_2$—($C_3$-$C_{10}$ cycloalkyl), —S(O)$_2$—(CH$_2$)$_t$($C_6$-$C_{10}$ aryl), —S(O)$_2$—(CH$_2$)$_t$(5-10 membered heteroaryl), —S(O)$_2$—(CH$_2$)$_t$($C_3$-$C_{10}$ cycloalkyl), and —S(O)$_2$—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. The term substituted sulfonyl includes the groups alkylsulfonyl, substituted alkylsulfonyl, cycloalkylsulfonyl, substituted cycloalkylsulfonyl, arylsulfonyl and heteroarylsulfonyl.

'Alkylsulfonyl' refers to a radical —S(O)$_2$R$^{89}$ where R$^{89}$ is an $C_1$-$C_8$ alkyl group as defined herein. Representative examples include, but are not limited to, methylsulfonyl, ethylsulfonyl, propylsulfonyl and butylsulfonyl.

'Substituted Alkylsulfonyl' refers to a radical —S(O)$_2$R$^{90}$ where R$^{90}$ is an $C_1$-$C_8$ alkyl group as defined herein, substituted with halo, substituted or unsubstituted amino, or hydroxy.

'Cycloalkylsulfonyl' refers to a radical —S(O)$_2$R$^{91}$ where R$^{91}$ is a $C_3$-$C_{10}$ cycloalkyl or group as defined herein. Representative examples include, but are not limited to, cyclopropylsulfonyl, cyclohexylsulfonyl, and cyclopentylsulfonyl.

'Substituted cycloalkylsulfonyl' refers to the group —S(O)$_2$R$^{92}$ where R$^{92}$ is a $C_3$-$C_{10}$ cycloalkyl, substituted with halo, substituted or unsubstituted amino, or hydroxy.

'Arylsulfonyl' refers to a radical —S(O)$_2$R$^{93}$ where R$^{93}$ is an $C_6$-$C_{10}$ aryl group as defined herein.

'Heteroarylsulfonyl' refers to a radical —S(O)$_2$R$^{94}$ where R$^{94}$ is an 5-10 membered heteroaryl group as defined herein.

'Sulfo' or 'sulfonic acid' refers to a radical such as —SO$_3$H.

'Substituted sulfo' or 'sulfonic acid ester' refers to the group —S(O)$_2$OR$^{95}$, wherein R$^{95}$ is selected from:

$C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or $C_1$-$C_8$ alkyl substituted with halo, substituted or unsubstituted amino, or hydroxy; or —$C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'Substituted sulfo' or 'sulfonic acid ester' groups are —S(O)$_2$—O—($C_1$-$C_8$ alkyl) and —S(O)$_2$—O—($C_3$-$C_{10}$ cycloalkyl), —S(O)$_2$—O—(CH$_2$)$_t$($C_6$-$C_{10}$ aryl), —S(O)$_2$—O—(CH$_2$)$_t$(5-10 membered heteroaryl), —S(O)$_2$—O—(CH$_2$)$_t$($C_3$-$C_{10}$ cycloalkyl), and —S(O)$_2$—O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Thiol' refers to the group —SH.

'Aminocarbonylamino' refers to the group —NR$^{96}$C(O)NR$^{96}$R$^{96}$ where each R$^{96}$ is independently hydrogen $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl, as defined herein; or where two R$^{96}$ groups, when attached to the same N, are joined to form an alkylene group.

'Bicycloaryl' refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

'Bicycloheteroaryl' refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

'Compounds of the present invention', and equivalent expressions, are meant to embrace the compounds as hereinbefore described, in particular compounds according to any of the formulae herein recited and/or described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

'Cycloalkylalkyl' refers to a radical in which a cycloalkyl group is substituted for a hydrogen atom of an alkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

'Heterocycloalkylalkyl' refers to a radical in which a heterocycloalkyl group is substituted for a hydrogen atom of an alkyl group. Typical heterocycloalkylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

'Cycloalkenyl' refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

'Substituted cycloalkenyl' refers to those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Fused Cycloalkenyl' refers to a cycloalkenyl having two of its ring carbon atoms in common with a second aliphatic or aromatic ring and having its olefinic unsaturation located to impart aromaticity to the cycloalkenyl ring.

'Ethenyl' refers to substituted or unsubstituted —(C=C)—.

'Ethylene' refers to substituted or unsubstituted —(C—C)—.

'Ethynyl' refers to —(C≡C)—.

'Hydrogen bond donor' group refers to a group containg O—H, or N—H functionality. Examples of 'hydrogen bond donor' groups include —OH, —NH$_2$, and —NH—R$^{97}$ and wherein R$^{97}$ is alkyl, acyl, cycloalkyl, aryl, or heteroaryl.

'Dihydroxyphosphoryl' refers to the radical —PO(OH)$_2$.

'Substituted dihydroxyphosphoryl' refers to those groups recited in the definition of "substituted" herein, and particularly refers to a dihydroxyphosphoryl radical wherein one or both of the hydroxyl groups are substituted. Suitable substituents are described in detail below.

'Aminohydroxyphosphoryl' refers to the radical —PO(OH)NH$_2$.

'Substituted aminohydroxyphosphoryl' refers to those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

'Nitrogen-Containing Heterocycloalkyl' group means a 4 to 7 membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

'Thioketo' refers to the group =S.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The 'therapeutically effective amount' can vary depending on the compound, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

'Compounds of the present invention', and equivalent expressions, are meant to embrace compounds of the Formula (e) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

When ranges are referred to herein, for example but without limitation, $C_1$-$C_8$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or =substituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radio-isotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure S-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The compounds of this invention may possess one or more asymmetric centers; such compounds can therefore be produced as individual (R)- or (S)-stereoisomers or as mixtures thereof.

"Full Agonist" refers to a compound that binds (has affinity for) and activates a receptor, displaying substantially full efficacy at that receptor. One example of a drug that acts as a full agonist is isoproterenol, which mimics the action of adrenaline at β adrenoreceptors. Another example is morphine, which mimics the actions of endorphins at μ-opioid receptors throughout the central nervous system. A "full agonist" may be distinguished from a "partial agonist" (such as buspirone, aripiprazole, buprenorphine, or norclozapine) that also binds and activates a given receptor, but has only partial efficacy at the receptor relative to a full agonist. One study of benzodiazepine active sedative hypnotics found that partial agonists may have just under half the strength of full agonists.

"An additional α-adrenergic modulator" refers to a compound that binds or has affinity for an α-adrenergeric receptor or adrenoceptor and serves to modulate the activity of that receptor either as a full agonist, a partial agonist, a full antagonist or a partial antagonist.

"Enzymatically cleavable group" refers to a functional group that, in the presence of one or more enzymes, may be removed or separated from the remaining part of a molecule. Representative examples include esters with carboxylic acids. Particular examples include esters with amino acids.

Mood disorder is the term given for a group of diagnoses in the Diagnostic and Statistical Manual of Mental Disorders (DSM IV TR) classification system where a disturbance in the person's mood is hypothesized to be the main underlying feature. The classification is known as mood (affective) disorders in ICD 10. Two groups of mood disorders are broadly recognized; the division is based on whether the person has ever had a manic or hypomanic episode. Thus, there are depressive disorders, of which the best known and most researched is major depressive disorder (MDD) commonly called clinical depression or major depression, and bipolar disorder (BD), formerly known as "manic depression" and described by intermittent periods of manic and depressed episodes.

Depressive disorders include "Major depressive disorder (MDD)" commonly called major depression, unipolar depression, or clinical depression, where a person has two or more major depressive episodes. Depression without periods of mania is sometimes referred to as unipolar depression because the mood remains at one emotional state or "pole". Diagnosticians recognize several subtypes or course specifiers: Atypical depression (AD) is characterized by mood reactivity (paradoxical anhedonia) and positivity, significant weight gain or increased appetite ("comfort eating"), excessive sleep or somnolence (hypersomnia), a sensation of heaviness in limbs known as leaden paralysis, and significant social impairment as a consequence of hypersensitivity to perceived interpersonal rejection. Difficulties in measuring this subtype have led to questions of its validity and prevalence. Melancholic depression is characterized by a loss of pleasure (anhedonia) in most or all activities, a failure of reactivity to pleasurable stimuli, a quality of depressed mood more pronounced than that of grief or loss, a worsening of symptoms in the morning hours, early morning waking, psychomotor retardation, excessive weight loss (not to be confused with anorexia nervosa), or excessive guilt. Psychotic major depression (PMD), or simply psychotic depression, is the term for a major depressive episode, particularly of melancholic nature, where the patient experiences psychotic symptoms such as delusions or, less commonly, hallucinations. These are most commonly mood-congruent (content coincident with depressive themes). Catatonic depression is a rare and severe form of major depression involving disturbances of motor behavior and other symptoms. Here the person is mute and almost stuporose, and either immobile or exhibits purposeless or even bizarre movements. Catatonic symptoms also occur in schizophrenia, a manic episode, or be due to neuroleptic malignant syndrome. Postpartum depression (PPD) is listed as a course specifier in DSM-IV-TR; it refers to the intense, sustained and sometimes disabling depression experienced by women after giving birth. Postpartum depression, which has incidence rate of 10-15%, typically sets in within three months of labor, and lasts as long as three months. Seasonal affective disorder (SAD), also known as "winter depression" or "winter blues", is a specifier. Some people have a seasonal pattern, with depressive episodes coming on in the autumn or winter, and resolving in spring. The diagnosis is made if at least two episodes have occurred in colder months with none at other times over a two-year period or longer. Some such patients may display suicidal behavior.

Dysthymia, which is a chronic, different mood disturbance where a person reports a low mood almost daily over a span of at least two years. The symptoms are not as severe as those for major depression, although people with dysthymia are vulnerable to secondary episodes of major depression (sometimes referred to as double depression). Depressive Disorder Not Otherwise Specified (DD-NOS) is designated by the code 311 for depressive disorders that are impairing but do not fit any of the officially specified diagnoses. According to the DSM-IV, DD-NOS encompasses "any depressive disorder that does not meet the criteria for a specific disorder." It includes the research diagnoses of recurrent brief depression, and minor depressive disorder listed below. Recurrent brief depression (RBD), distinguished from major depressive disorder primarily by differences in duration. People with RBD have depressive episodes about once per month, with individual episodes lasting less than two weeks and typically less than 2-3 days. Diagnosis of RBD requires that the episodes occur over the span of at least one year and, in female patients, independently of the menstrual cycle.[ People with clinical depression can develop RBD, and vice versa, and both illnesses have similar risks. Minor depressive disorder, or simply minor depression, which refers to a depression that does not meet full criteria for major depression but in which at least two symptoms are present for two weeks.

Bipolar disorder (BD), a mood disorder formerly known as "manic depression" and described by alternating periods of mania and depression (and in some cases rapid cycling, mixed states, and psychotic symptoms). Subtypes include: Bipolar I is distinguished by the presence or history of one or more manic episodes or mixed episodes with or without major depressive episodes. A depressive episode is not required for the diagnosis of Bipolar I disorder, but depressive episodes are often part of the course of the illness. Cyclothymia is a different form of bipolar disorder, consisting of recurrent hypomanic and dysthymic episodes, but no full manic episodes or full major depressive episodes. Bipolar Disorder Not Otherwise Specified (BD-NOS), sometimes called "sub-threshold" bipolar, indicates that the patient suffers from some symptoms in the bipolar spectrum (e.g. manic and depressive symptoms) but does not fully qualify for any of the three formal bipolar DSM-IV diagnoses mentioned above. It is estimated that roughly one percent of the adult population suffers from bipolar I, roughly one percent of the adult population suffers from bipolar II or cyclothymia, and somewhere between two and five percent suffer from "sub-threshold" forms of bipolar disorder.

Substance-induced mood disorders refers to a mood disorder that can be classified as substance-induced if its etiology can be traced to the direct physiologic effects of a psychoactive drug or other chemical substance, or if the development of the mood disorder occurred contemporaneously with substance intoxication or withdrawal. Alternately, an individual may have a mood disorder coexisting with a substance abuse disorder. Substance-induced mood disorders can have features of a manic, hypomanic, mixed, or depressive episode. Most substances can induce a variety of mood disorders. For example, stimulants such as amphetamine (Adderall, Dexedrine; "Speed"), methamphetamine (Desoxyn; "Meth", "Crank", "Crystal", etc), and cocaine ("Coke", "Crack", etc) can cause manic, hypomanic, mixed, and depressive episodes. Alcohol-induced mood disorders includes major depressive disorder occurring in heavy drinkers and those with alcoholism. Controversy has previously surrounded whether those who abused alcohol and developed depression were self-medicating their pre-existing depression, but recent research has concluded that, while this may be true in some cases, alcohol misuse directly causes the development of depression in a significant number of heavy drinkers. High rates of suicide also occur in those who have alcohol-related problems. It is usually possible to differentiate between alcohol-related depression and depression which is not related to alcohol intake by taking a careful history of the patient. Depression and other mental health problems associated with alcohol misuse may be due to distortion of brain chemistry, as they tend to improve on their own after a period of abstinence.

Benzodiazepine-induced mood disorders may be associated with long term use of benzodiazepines which have a similar effect on the brain as alcohol and are also associated with depression. Major depressive disorder can also develop as a result of chronic use of benzodiazepines or as part of a protracted withdrawal syndrome. Benzodiazepines are a class of medication which are commonly used to treat insomnia, anxiety and muscular spasms. As with alcohol, the effects of benzodiazepine on neurochemistry, such as decreased levels of serotonin and norepinephrine, are believed to be responsible for the increased depression. Major depressive disorder may also occur as part of the benzodiazepine withdrawal syndrome. In a long-term follow-up study of patients dependent on benzodiazepines, it was found that 10 people (20%) had taken drug overdoses while on chronic benzodiazepine medication despite only two people ever having had any pre-existing depressive disorder. A year after a gradual withdrawal program, no patients had taken any further overdoses. Depression resulting from withdrawal from benzodiazepines usually subsides after a few months but in some cases may persist for 6-12 months.

Anxiety disorder is a blanket term covering several different forms of abnormal and pathological fear and anxiety which only came under the aegis of psychiatry at the very end of the 19th century. Current psychiatric diagnostic criteria recognize a wide variety of anxiety disorders. Recent surveys have found that as many as 18% of Americans may be affected by one or more of them.

Anxiety disorders are often debilitating chronic conditions, which can be present from an early age or begin suddenly after a triggering event. They are prone to flare up at times of high stress and are frequently accompanied by physiological symptoms such as headache, sweating, muscle spasms, palpitations, and hypertension, which in some cases lead to fatigue or even exhaustion.

Although in casual discourse the words anxiety and fear are often used interchangeably, in clinical usage, they have distinct meanings; anxiety is defined as an unpleasant emotional state for which the cause is either not readily identified or perceived to be uncontrollable or unavoidable, whereas fear is an emotional and physiological response to a recognized external threat. The term anxiety disorder, however, includes fears (phobias) as well as anxieties. Anxiety disorders are often comorbid with other mental disorders, particularly clinical depression, which may occur in as many as 60% of people with anxiety disorders. The fact that there is considerable overlap between symptoms of anxiety and depression, and that the same environmental triggers can provoke symptoms in either condition, may help to explain this high rate of comorbidity.

Types of anxiety disorders include generalized anxiety disorder, panic disorder, phobias, agoraphobia, social anxiety disorder, obsessive-compulsive disorder, post-traumatic stress disorder, and separation anxiety disorder.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Compositions

Pharmaceutical compositions, having potency, specificity and selectivity in the diagnosis, prophylaxis, prevention, treatment, relatively rapid treatment and prognosis of conditions such mood disorders, including for instance, major depression and dysthymia, anxiety and other related conditions are described herein. Such compositions may be useful, for example, in reducing frequency of suicide or deterring or averting an imminent suicide.

Accordingly, the invention provides pharmaceutical compositions to treat an anxiety disorder or a mood disorder comprising an inhibitor of α-adrenergic receptor and two or more inhibitors of central stress nuclei.

The invention further provides pharmaceutical compositions to treat an anxiety disorder or a mood disorder comprising:
 a) a full agonist of α1- and α2-adrenoceptor;
 b) a glucocorticoid receptor agonist;
 c) a serotonergic 5HT1A receptor agonist; and
 d) a carrier or adjuvant.

The invention further provides pharmaceutical compositions to treat an anxiety disorder or a mood disorder comprising:
 a) a prodrug of a full agonist of α1- and α2-adrenoceptor;
 b) a glucocorticoid receptor agonist;
 c) a serotonergic 5HT1A receptor agonist; and
 d) a carrier or adjuvant.

The invention further provides pharmaceutical compositions to treat an anxiety disorder or a mood disorder comprising:
 a) a full agonist or a prodrug of a full agonist of α1- and α2-adrenoceptor;
 b) a glucocorticoid receptor agonist;
 c) a serotonergic 5HT1A receptor agonist;
 d) an additional α-adrenergic modulator; and
 e) a carrier or adjuvant.

In one embodiment, with respect to the pharmaceutical composition, the modulator of α1- and α2-adrenoceptor is a full agonist of both α1- and α2-adrenoceptor.

In one particular embodiment, with respect to the pharmaceutical composition, the modulator of α1- and α2-adrenoceptor is an epinephrine derivative. Another particular embodiment, modulator of α1- and α2-adrenoceptor is a norepinephrine derivative.

In a more particular embodiment, with respect to the pharmaceutical composition, the modulator of α1- and α2-adrenoceptor is 6-fluoronorepinephrine.

In another embodiment, the invention provides pharmaceutical compositions comprising:
 a) a prodrug of a full agonist of α1- and α2-adrenoceptor
 b) a glucocorticoid receptor agonist;
 c) a serotonergic 5HT1 A receptor agonist;
 d) an additional α-adrenergic modulator; and
 e) a carrier or adjuvant.

In another embodiment, the invention provides pharmaceutical compositions comprising:
 a) a prodrug of a 6-fluoronorepinephrine;
 b) a glucocorticoid receptor agonist;
 c) a serotonergic 5HT1A receptor agonist;
 d) an additional α-adrenergic modulator; and
 e) a carrier or adjuvant.

In one embodiment, with respect to the pharmaceutical composition of the invention the adrenoceptor agonist or the inhibitor of the adrenergic receptor is a compound according to formula I:

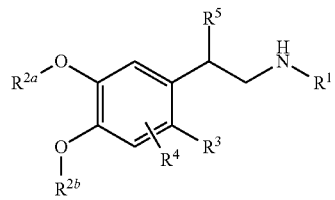

I wherein
 $R^1$ is selected from H, and substituted or unsubstituted $C_1$-$C_6$ alkyl;
 each $R^{2a}$, and $R^{2b}$ is independently selected from H, and an enzymatically cleavable group;
 each $R^3$ and $R^4$ is independently selected from H, halo, substituted or unsubstituted $C_1$-$C_6$ alkyl, substituted or unsubstituted halo $C_1$-$C_6$ alkyl, hydroxy, amino, and $C_1$-$C_6$ alkoxy; $R^5$ is H, or OH;

or a pharmaceutically acceptable salt, or solvate thereof; and stereoisomers, isotopic variants and tautomers thereof.

In one embodiment, with respect to the pharmaceutical composition of the invention, the adrenoceptor agonist or the inhibitor of the adrenergic receptor is a compound according to formula I; and $R^1$ is H, Me, Et, n-Pr, i-Pr, n-Bu, t-Bu, or $CF_3$. In another embodiment, $R^1$ is Me. In a particular embodiment, $R^1$ is H.

In one embodiment, with respect to the compound of the formula I, $R^4$ is H.

In one embodiment, with respect to the compound of the formula I, $R^3$ is H, F, Cl, or $CF_3$. In another embodiment, $R^3$ is Me or $NMe_2$. In a particular embodiment, $R^3$ is F.

In one embodiment, with respect to the compound of the formula I, $R^5$ is H.

In one embodiment, with respect to the compound of the formula I, $R^5$ is OH.

In one embodiment, with respect to the pharmaceutical composition of the invention, the adrenoceptor agonist or the inhibitor of the adrenergic receptor is a compound according to formula IIa or IIb or IIc:

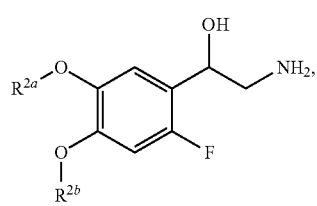

IIa

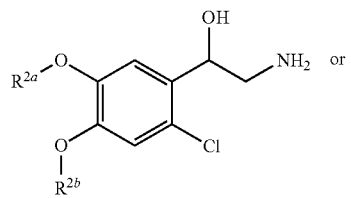

IIb or

-continued

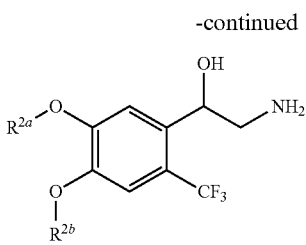

IIc wherein
each $R^{2a}$, and $R^{2b}$ is independently selected from H, and an enzymatically cleavable group;
or a pharmaceutically acceptable salt, or solvate thereof; and stereoisomers, isotopic variants and tautomers thereof.

In one embodiment, with respect to the pharmaceutical composition of the invention, the adrenoceptor agonist or the inhibitor of the adrenergic receptor is a compound according to formulae I-IIc; and each of $R^{2a}$, and $R^{2b}$ is H.

In one embodiment, with respect to the compound according to formulae I-IIc; and at least one of $R^{2a}$, and $R^{2b}$ is other than H.

In one embodiment, with respect to the compound according to formulae I-IIc; and $R^{2a}$ is H; and $R^{2b}$ is an enzymatically cleavable group.

In one embodiment, with respect to the compound according to formulae I-IIc; and $R^{2b}$ is H; and $R^{2a}$ is an enzymatically cleavable group.

In one embodiment, with respect to the compound according to formulae I-IIc; and each $R^{2a}$ and $R^{2b}$ is independently an enzymatically cleavable group.

In one embodiment, with respect to the compound according to formulae I-IIc, each $R^{2a}$ and $R^{2b}$ is independently H, or an enzymatically cleavable group; and the enzymatically cleavable group is selected from
substituted or unsubstituted $C_1$-$C_6$ acyl, an amino acid residue, a dipeptide residue, a tripeptide residue, and a group

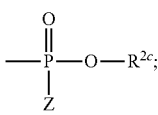

$R^{2'}$ is alkyl, aryl, or heteroaryl; Z is an amino acid residue, a dipeptide residue, or a tripeptide residue.

In one embodiment, with respect to the compound according to formulae I-IIc, each $R^{2a}$ and $R^{2b}$ is independently H or an enzymatically cleavable group; and the enzymatically cleavable group is an amino acid residue.

In one embodiment, with respect to the compound according to formulae I-IIc, each $R^{2a}$ and $R^{2b}$ is independently H, or an enzymatically cleavable group; and the enzymatically cleavable group is selected from -D-isoleucyl; -L-isoleucyl; -D-valy; -L-valyl; -glycyl; -D-phenylalanyl; -L-phenylalanyl; -D-leucyl; -L-leucyl; -L-aspartyl; -D-alpha-aspartyl; -L-alpha-aspartyl; -D-beta-aspartyl; -L-beta-aspartyl; and -L-prolyl.

In one embodiment, with respect to the compound according to formulae I-IIc, each $R^{2a}$ and $R^{2b}$ is independently H, or an enzymatically cleavable group; and the enzymatically cleavable group is a dipeptide residue.

In one embodiment, with respect to the compound according to formulae I-IIc, each $R^{2a}$ and $R^{2b}$ is independently H, or an enzymatically cleavable group; and the enzymatically cleavable group is a tripeptide residue.

In one embodiment, with respect to the compound according to formulae I-IIc, each $R^{2a}$ and $R^{2b}$ is independently H, or an enzymatically cleavable group; and the enzymatically cleavable group is

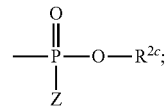

and wherein Z and $R^{2c}$ are as in claim 2.

In one embodiment, with respect to the compound according to formulae I-IIc, each $R^{2a}$ and $R^{2b}$ is independently H, an enzymatically cleavable group, the enzymatically cleavable group is as described above; and Z is an amino acid residue.

In one embodiment, with respect to the compound according to formulae I-IIc, each $R^{2a}$ and $R^{2b}$ is independently H, an enzymatically cleavable group, the enzymatically cleavable group is as described above; and $R^{2c}$ is benzyl.

In one embodiment, with respect to the compound according to formulae I-IIc, each $R^{2a}$ and $R^{2b}$ is independently H, an enzymatically cleavable group; and the enzymatically cleavable group is the enzymatically cleavable group is selected from -D-isoleucyl phosphoramidate; -L-isoleucyl phosphoramidate; -D-valyl phosphoramidate; -L-valyl phosphoramidate; -glycyl phosphoramidate; -D-phenylalanyl phosphoramidate; -L-phenylalanyl phosphoramidate; 5'-0-L-leucyl phosphoramidate; 5'-0-L-aspartyl phosphoramidate; -D-alpha-aspartyl phosphoramidate; -L-alpha-aspartyl phosphoramidate; D-beta-aspartyl phosphoramidate; -L-beta-aspartyl phosphoramidate; and -L-prolyl phosphoramidate.

In one embodiment, with respect to the compound according to formulae I-IIc, each $R^{2a}$ and $R^{2b}$ is independently H, an enzymatically cleavable group; and the enzymatically cleavable group is substituted or unsubstituted $C_1$-$C_6$ acyl.

In one embodiment, with respect to the compound according to formulae I-IIc, each $R^{2a}$ and $R^{2b}$ is independently H, an enzymatically cleavable group; and the enzymatically cleavable group is COMe, COEt, CO-n-Pr, CO-i-Pr, or CO-t-Bu.

In one embodiment, with respect to the compound according to formulae I-IIc, each $R^{2a}$ and $R^{2b}$ is independently H, an enzymatically cleavable group; and the enzymatically cleavable group is CO-t-Bu.

In one embodiment, with respect to the pharmaceutical composition of the invention, the adrenoceptor agonist or the inhibitor of the adrenergic receptor is a compound according to formula IIIa, IIIb, or IIIc:

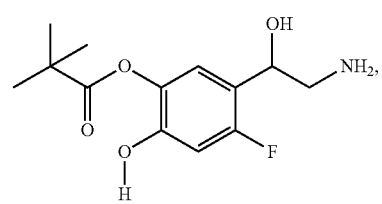

IIIa

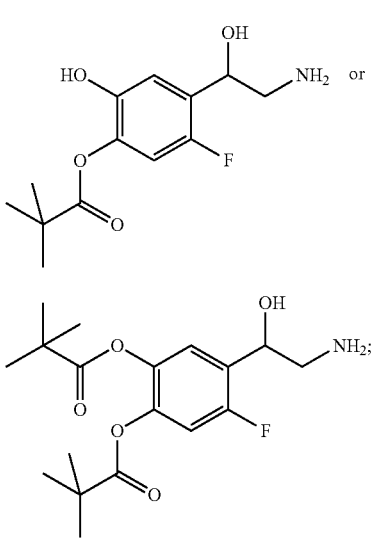

or a pharmaceutically acceptable salt, or solvate thereof; and stereoisomers, isotopic variants and tautomers thereof.

In one embodiment, with respect to the pharmaceutical composition of the invention, the adrenoceptor agonist or the inhibitor of the adrenergic receptor is a prodrug, and the prodrug is according to formula IIIc.

In one embodiment, with respect to the pharmaceutical composition of the invention, the prodrug does pass the blood-brain barrier. In one particular embodiment, with respect to the pharmaceutical composition of the invention, the prodrug does pass the blood-brain barrier and is enzymatically cleaved within the brain tho yield the active parent catecholamine.

In one embodiment, with respect to the pharmaceutical composition of the invention, the adrenoceptor agonist or the inhibitor of the adrenergic receptor is dp6FNE.

In one embodiment, with respect to the pharmaceutical composition of the invention, the adrenoceptor agonist or the inhibitor of the adrenergic receptor is dipiverfrin; provided that the composition further comprises an antagonist of beta adrenergic receptor.

In one embodiment, with respect to the pharmaceutical composition of the invention, the 5HT1A receptor agonist is 8-OHDPAT or 8-hydroxy-N,N-dipropyl-2-aminotetralin.

In one embodiment, with respect to the pharmaceutical composition of the invention, the 5HT1A receptor agonist is repinotan.

In one embodiment, with respect to the pharmaceutical composition of the invention, the 5HT1A receptor agonist is azapirone such as buspirone, gepirone, and tandospirone.

In one embodiment, with respect to the pharmaceutical composition of the invention, the 5HT1A receptor agonist is buspirone, gepirone, or tandospirone.

In one embodiment, with respect to the pharmaceutical composition of the invention, the glucocorticoid receptor agonist is corticosterone.

In one embodiment, with respect to the pharmaceutical composition of the invention, the glucocorticoid receptor agonist is dexamethasone.

In one embodiment, with respect to the pharmaceutical composition of the invention, the additional α-adrenergic modulator is a compound capable of blocking activation of cardiovascular a1-adrenoceptor.

In one embodiment, with respect to the pharmaceutical composition of the invention, the additional α-adrenergic modulator is an α-adrenergic antagonist. In one embodiment, with respect to the pharmaceutical composition of the invention, the additional α-adrenergic modulator is selected from doxazosin, terazosin, labetalol, indoramin, phenoxybenzamine, tolazoline, and dihydroergotamine. In one particular embodiment, with respect to the pharmaceutical composition of the invention, the additional α-adrenergic modulator is a modulator incapable of crossing the blood-brain barrier. In another particular embodiment, with respect to the pharmaceutical composition of the invention, the additional α-adrenergic modulator is a modulator which does not enter the brain. In a more particular embodiment, with respect to the pharmaceutical composition of the invention, the additional α-adrenergic modulator is prazosin. In one embodiment, with respect to the pharmaceutical compositions of the invention, the additional α-adrenergic modulator is present at dosage levels equivalent to 0.1 to 100% of the dosage normally administered in a monotherapy regimen. In one embodiment, with respect to the pharmaceutical composition of the invention, the additional α-adrenergic modulator is present at dosage levels equivalent to about 0.5 to about 2 mg of the dose. In one embodiment, with respect to the pharmaceutical composition of the invention, the additional α-adrenergic modulator is present at dosage levels equivalent to about 0.5 to about 2 mg of the dose and is administered twice daily. One example of such an additional α-adrenergic modulator is carvedilol.

In one embodiment, with respect to the pharmaceutical composition of the invention, the carrier is a parenteral carrier. In one embodiment, with respect to the pharmaceutical composition of the invention, the carrier is an oral carrier. In one embodiment, with respect to the pharmaceutical composition of the invention, the carrier is a topical carrier.

In another aspect, the invention provides a method for treating α-adrenergic mediated disease or condition in a mammal comprising the step of administering to said mammal a composition of the invention. In one embodiment, the disease or condition is depression. In a particular aspect, the invention provides a use of the composition of the invention in antidepressant, anti-stress, or anxiolytic therapies. In a particular aspect, the invention provides a use of the composition of the invention in the rapid treatment of depression.

In another aspect, the invention provides a method for treating a disease selected from the group consisting of an anxiety disorder or a mood disorder in a mammal comprising the step of administering to said mammal a pharmaceutical composition according to the invention.

In one embodiment, with respect to the method, the disease is an anxiety disorder.

In one embodiment, with respect to the method, the disease is a mood disorder.

In one embodiment, with respect to the method, the mood disorder is selected from the group consisting of dysthymia and major depression.

In one embodiment, with respect to the method, the administering results in a reduction in at least one clinical symptom of depression within one day.

In one embodiment, with respect to the method, the administering results in a reduction in at least one clinical symptom of depression within one week.

In one embodiment, with respect to the method, the administering results in a reduction in at least one clinical symptom of depression within one month.

In one embodiment, with respect to the method, the administering results in reducing a neural response in a stress response.

In one embodiment, with respect to the method, the administering results in increasing neural activity in one or more areas of the brain involved in motivated behavior.

In one embodiment, the administering results in a reduction in the frequency of suicide, deterring suicide or preventing imminent suicide.

In a particular aspect, the invention provides pharmaceutical compositions comprising:
a) dp6FNE;
b) a glucocorticoid receptor agonist;
c) a serotonergic 5HT1A receptor agonist;
d) an additional α-adrenergic modulator; and
e) a carrier or adjuvant.

In another particular aspect, the invention provides a method to treat depression or mood disorder using pharmaceutical compositions comprising:
a) dp6FNE;
b) a glucocorticoid receptor agonist;
c) a serotonergic 51-1T1A receptor agonist;
d) an additional α-adrenergic modulator; and
e) a carrier or adjuvant.

In a particular embodiment, with respect to above pharmaceutical compositions, the composition comprises: dp6FNE, dexamethasone or corticosterone, 8-OHDPAT, prazosin, and a carrier or adjuvant.

In a particular embodiment, with respect to above pharmaceutical compositions, the composition comprises: low doses of dp6FNE, dexamethasone or corticosterone, 8-OHDPAT, prazosin, and a carrier or adjuvant.

In a particular aspect, the present invention provides a novel form of antidepressant and anti-stress medication that is based on the selective inhibition of central stress circuits by combined low-dose agonist stimulation of various inhibitory, autoreceptors concentrated on stress neurons. In one embodiment, the low-dose agonists are noradrenergic, serotonergic and PVH-HPA agonists. In one particular embodiment, the low-dose agonists or inhibitors may be dp6FNE, 8-OHDPAT, or dexamethasone.

In a particular aspect, the present invention provides a novel concept that depressive illness is mediated by a conglomeration of separate activated central stress circuits and is best treated with a corresponding mixture of separate agonists for inhibitory receptors in each of the activated stress regions. The invention represents a rational method to achieve high efficacy and rapid onset of action with minimum side effects. In one embodiment, the central stress circuits are the unique high sensitivity of inhibitory autoreceptors in each of the stress regions.

In one embodiment, with respect to the pharmaceutical compositions or the methods of the invention, the cocktail of inhibitors or agonists have a greater initial efficacy. In another embodiment, the cocktail has a faster onset of the action. In another embodiment, the cocktail is in low-dosage forms.

Additional embodiments within the scope of the present invention are set forth in non-limiting fashion elsewhere herein and in the examples. It should be understood that these examples are for illustrative purposes only and are not to be construed as limiting this invention in any manner.

In certain aspects, the present invention provides prodrugs according to the formulae I-IIIc. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholinyl esters and the like.

Certain compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy) alkylesters. Preferred are the $C_1$ to $C_8$ or $C_1$-$C_6$alkyl, $C_2$-$C_8$ alkenyl, aryl, substituted aryl, and arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound. In certain embodiments, the pharmaceutical composition may comprise a compound of the invention in combination with one or more compounds or compositions of like therapeutic utility and effect.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable, oral or intranasal compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Intranasal compositions are typically mucoadhesive temperature-mediated in situ gel formulations using chitosan and hydroxyl propyl methylcellulose which enhance intranasal fixation and absorption producing transport into the central nervous system Khan, S., Patil, K., Bobade, N., Yeole, P., Gaikwad, R. 2010. Formulation of intranasal mucoadhesive temperature-mediated in situ gel containing ropinirole and evaluation of brain targeting efficiency in rats. *J Drug Target* 18, 223-234.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's *The Science and Practice of Pharmacy*, 21$^{st}$ edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences*.

The following formulation examples illustrate representative pharmaceutical compositions that may be prepared in accordance with this invention. The present invention, however, is not limited to the following pharmaceutical compositions.

Formulation 1

Tablets

The components of the pharmaceutical composition of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2

Capsules

The components of the pharmaceutical composition of the invention may be admixed as a dry powder with a starch diluent in an approximate 1:1 weight ratio. The mixture is filled into 250 mg capsules (125 mg of active compound per capsule).

Formulation 3

Liquid

The components of the pharmaceutical composition of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4

Tablets

The components of the pharmaceutical composition of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5

Injection

The components of the pharmaceutical composition of the invention may be dissolved or suspended in a buffered sterile saline injectable aqueous medium to a concentration of approximately 5 mg/mL.

Formulation 6

Topical

Stearyl alcohol (250 g) and a white petrolatum (250 g) may be melted at about 75° C. and then a mixture of a the components of the pharmaceutical composition of the invention (50 g, in proper ratio) methylparaben (0.25 g), propylparaben (0.15 g), sodium lauryl sulfate (10 g), and propylene glycol (120 g) dissolved in water (about 370 g) is added and the resulting mixture is stirred until it congeals.

Formulation 7

Intranasal

Temperature-mediated in situ gelling systems are prepared by dissolving The components of the pharmaceutical composition of the invention, chitosan HCl (1% w/v) and HPMC (varying grades and concentrations) in 0.5% sodium chloride maintained at temperature ~4° C. To the resulting solution 1 mL 0.282 M sodium β-glycerophosphate solution (ultimate concentration 8.8 wt %) is added drop by drop with continuous stirring while maintaining the temperature below 10° C. using the ice bath. Benzalkonium chloride (0.05% w/v) is added and pH adjusted to 7.0 using 1 M NaOH. A final volume of 10 mL is achieved with 0.5% sodium chloride. The formulations are stored below 10° C.

Methods of Treatment

The present pharmaceutical compositions of the invention are used as therapeutic agents for the treatment of conditions in mammals. Accordingly, the compounds and pharmaceutical compositions of this invention find use as therapeutics for preventing and/or treating illnesses, diseases, ailments, etc. such as, but not limited to, anxiety and mood disorders, such as, for instance depression and dysthymia.

In a method of treatment aspect, this invention provides a method of treating a mammal susceptible to or afflicted with a condition as recited above, which method comprises administering an effective amount of one or more of the pharmaceutical compositions described herein. In additional method of treatment aspects, this invention provides methods of treating a mammal susceptible to or afflicted with an anxiety or mood disorder, the method comprises administering an effective condition-treating or condition-preventing amount of one or more of the pharmaceutical compositions just described.

As a further aspect of the invention there is provided the present compounds for use as a pharmaceutical especially in the treatment or prevention of the aforementioned conditions and diseases. The applicants also provide the use of the present compounds in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as CNS conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg. Transdermal doses are generally selected to provide similar or lower blood levels than are achieved using injection doses.

The pharmaceutical compositions of this invention can be administered as the sole active composition or they can be administered in combination with other agents, including other active ingredients and derivatives.

General Synthetic Procedures

The compounds of formaulae I-IIIc can be prepared from readily available starting materials using the following general methods and procedures. See, e.g., Synthetic Scheme, below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds of formaulae I-IIIc, for example, may be prepared by the reaction of a chloro derivative with an appropriately substituted amine and the product isolated and purified by known standard procedures. Such procedures include (but are not limited to) recrystallization, column chromatography or HPLC. The following schemes are presented with details as to the preparation of representative fused heterocyclics that have been listed hereinabove. The compounds of the invention may be prepared from known or commercially available starting materials and reagents by one skilled in the art of organic synthesis.

The compounds of formaulae I-IIIc may be prepared by a variety of processes well known for the preparation of compounds of this type, for example reaction schemes. and general procedures as described below.

The syntheses of representative compounds of this invention are carried out in accordance with the methods set forth herein and using the appropriate reagents, starting materials, and purification methods known to those skilled in the art. All starting materials in the following general syntheses may be commercially available or obtained by conventional methods known to those skilled in the art.

In this specification, especially in "Representative Synthetic Methods", the following abbreviations can be used:

BEP 2-bromo-1-ethylpyridinium tetrafluoroborate
BOP benzotriazol-1-yloxy-tris(dimethylamino)phosphonium hexafluorophosphate
CDI 2-chloro-1,3-dimethylimidazolinium chloride
DCC dicyclohexylcarbodiimide
DCM dichloromethane
DME 1,2-dimethoxyethane, dimethoxyethane
DMF N,N-dimethylformamide
DMSO dimethyl sulfoxide
EDC 1-ethyl-3-(3'-dimethylaminopropyl)carbodiimide hydrogen chloride
EtOAc ethyl acetate
EtOH ethanol
HOBt 1-hydroxybenzotriazole
MeOH methanol
NMP N-methyl-2-pyrroliidone
THF tetrahydrofuran
TFA trifluoroacetic acid
uM $\mu$M
uL $\mu$L Synthesis of Representative Compounds of Formulae I-IIIc The compounds or starting materials for the compounds of formulae I-IIIc may be prepared following the various methods described in U.S. Pat. No. 3,904,671, U.S. Pat. No. 4,338,455, and WO8203327. These publications are incorporated by reference in their entirety, including all figures and tables, to the extent they are not inconsistent with the explicit teachings of this specification.

General Synthetic Methods for Preparing Compounds of Formulae I-IIIc
The compounds of formulae I-IIIc may be prepared following the representative synthetic schemes shown below:
Scheme 1
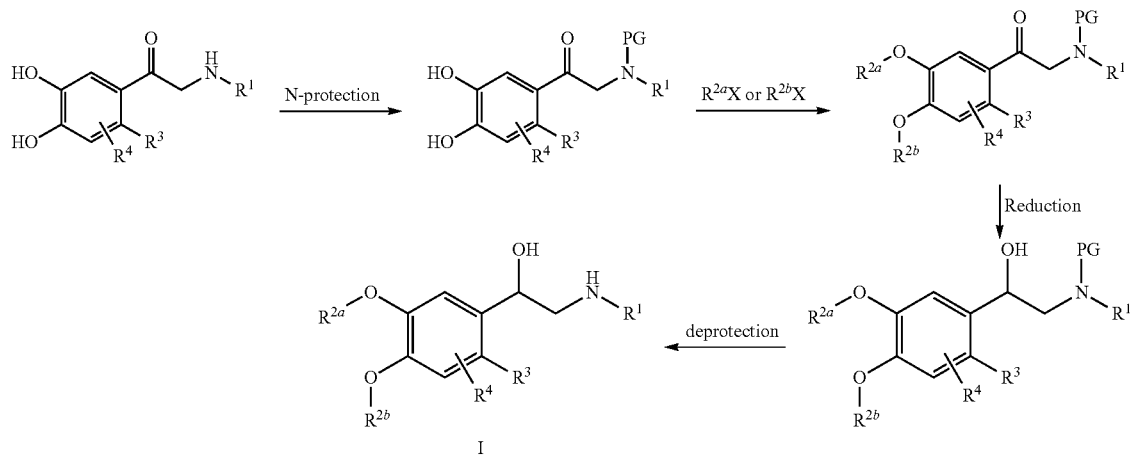
wherein $R^1$, $R^{2a}$, $R^{2b}$, $R^3$, and $R^4$ are as described herein; PG is a N-protecting group and X is a good leaving group. For example, X may be Cl, Br, I, or OTs.
Scheme 2
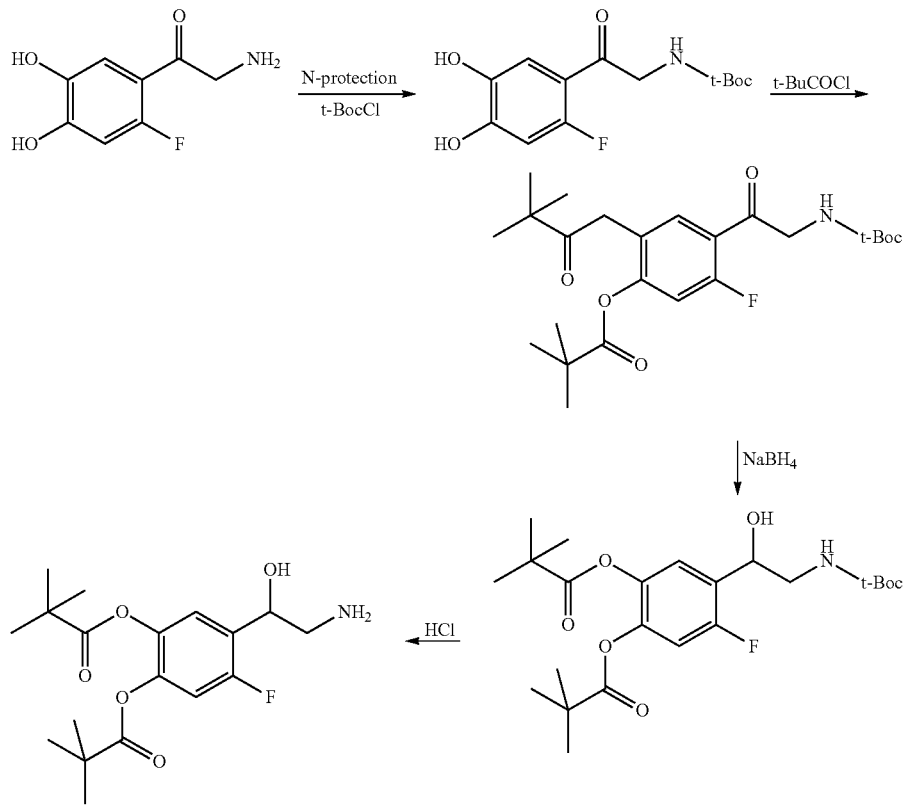

Scheme 3

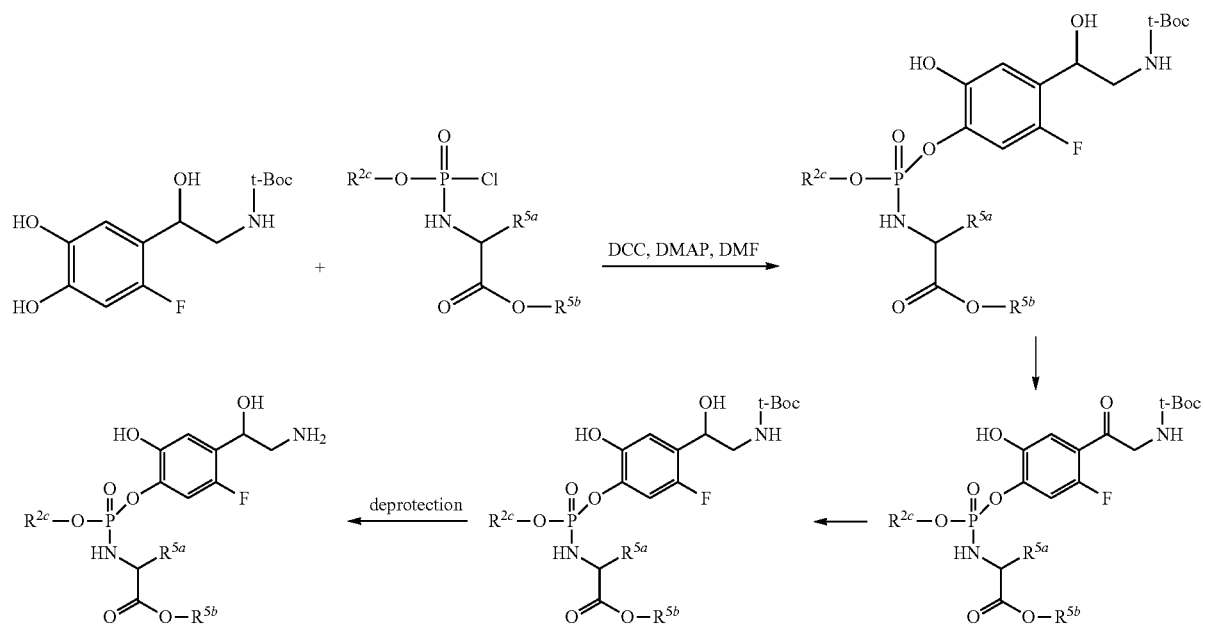

wherein and $R^{2c}$, $R^{5a}$, and $R^{5b}$ are independently H, or alkyl.

Therapeutic Effects

One of the drawbacks of antidepressant agents is their slowness of action. Most presently available drugs require several weeks administration before they produce clinically significant antidepressant effects (Sartorius et al., *International Journal of Neuropsychopharmacology* (2007) 10 Suppl 1: S1-207). This can be especially deleterious for agitated or suicidal patients who require immediate relief of symptoms and who may be resistant to psychotherapeutic or cognitive/behavioral-based interventions. However, it may be possible to address this problem with the use of drugs that selectively and rapidly inhibit central stress-sensitive brain areas known to be active during depression. Evidence has been mounting that major depressive illness is accompanied by the activation of a number of central stress areas including the amygdala (Mayberg, *Biological Psychiatry* (2007) 61: 729-730; Surget et al., *Neuropsychopharmacology* (2009) 34: 1363-1380), bed nucleus of the stria terminalis (Price et al., *Neuropsychopharmacology* (2010) 35: 192-216; Muigg et al., *Biological Psychiatry* (2007) 61: 783-796), paraventricular nucleus of the hypothalamus (Stout et al., *European Journal of Pharmacology* (2000) 401: 39-46); 2000; Stone et al., *Biological Psychiatry* (2006) 60: 803-811; Stone et al., *Progress in Neuropsychopharmacology and Biological Psychiatry* (2007) 31: 1196-1207; 2006; 2007; Muigg *Biological Psyciatry* (2007) 61:783-796) and locus coeruleus (Weiss et al., *Neuropeptides*, (2005) 39: 281-287; Stone et al. *Journal of Neuropsychopharmacology* (2010) In press). These findings have suggested that the activities of these stress areas underlie or exacerbate the behavioral and affective symptoms of the disorder (Stone et al., *Neuroscience and Biobehavioral Reviews* (2008a) 32: 508-524; Price et al., *Neuropsychopharmacology* (2010) 35: 192-216; Mayberg, *Biological Psychiatry* (2007) 61: 729-730). If correct, it should be possible to produce a rapid reduction of symptoms by acutely and selectively inhibiting these regions pharmacologically. Such an immediate action may be helpful in bridging the therapeutic gap before more slowly-acting antidepressants can produce a more permanent therapeutic changes.

Weiss et al. showed that inhibition of the locus coeruleus (LC), the main noradrenergic stress nucleus, produced immediate anti-immobility effects in a forced swim stress model potentiated by chronic traumatic tailshock stress (Simson, et al., *Neuropharmacology* 1986; 25: 385-389). These findings are confirmed by with the data provided herein regarding dipivalyl-6-fluoronorepinephrine (dp6FNE), a catecholamine pro-drug that stimulates the 2 chief α-adrenergic inhibitory autoreceptors of the LC (Stone et al., *Journal of Neuropsychopharmacology* (2010) In press). This drug, at or below 1 mg/kg, i.p., demonstrates immediate anti-immobility effects without motor stimulation or sedation in a model of chronic depression in mice (repeated forced swim) that is resistant to acute treatment with all other currently available antidepressants so far tested, including ketamine.

Figure 2:
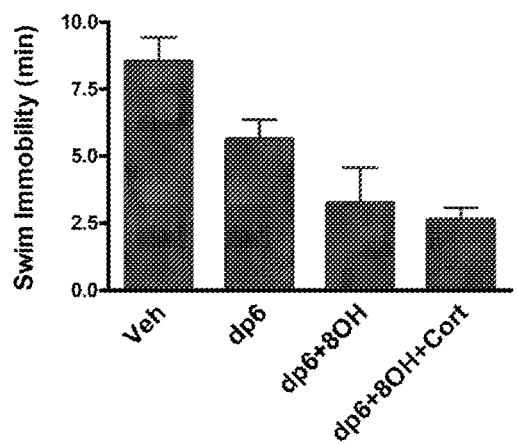
FIG. 2 shows the effect of co-administration of low i.p. doses of 8OHDPAT (0.05 mg/kg) and corticosterone (3 mg/kg) on anti-immobility effect of i.p. dp6FNE (1 mg/kg) in RFS test. Note progressive enhancement of antidepressant effect as raphe and PVH-HPA stress systems are inhibited along with LC (N=3).

In addition to noradrenergic-inhibiting agents, acute suppression of two other components of the stress circuit—the paraventricular hypothalamus (hypothalamo-pituitary-adrenal axis, PVH-HPA) with a low dose of the glucocorticoid receptor agonist, corticosterone (3 mg/kg, i.p.), and the serotonergic-raphe system with a low dose of the 5HT1A agonist, 8-OHDPAT (0.05 mg/kg, i.p.), produces rapid and effective preclinical antidepressant actions in a chronic depression model despite the partial desensitization of the glucocorticoid and 5HT1A receptors known to occur in depression (Greenberg et al., (1989) *Biol. Psychiatry* 26:530-532; López-Figueroa et al., (2004) *Biol. Psychiatry* 55:225-233). Furthermore, when these three agonists are combined at the above doses, their acute antidepressant actions summate or synergize to produce the most effective immediate response of any medication yet observed (FIG. 2). In addition to its obvious clinical implication, this demonstrates that depressive behavior is caused by a conglomeration of separate, active components of the stress circuit and, therefore, may be most effectively treated with a mixture of different selective inhibitory agonists at low doses rather than a single antidepressant at high dose. Such a strategy might maximize efficacy while minimizing side effects.

Producing an immediate, graded reduction in depression whose degree varies as a function of the fraction of the stress system that has been inhibited is desirable. Furthermore, the antidepressant effect so produced should be more rapid in onset than most currently available antidepressants, which may only target parts of this circuit or have less potent effects on it.

Inhibition of the noradrenergic, serotonergic and PVH-HPA axis system with a cocktail of drugs produces a beneficial effect and is more rapid in onset than the currently available antidepressants. The inhibitors may be dp6FNE (for noradrenergic), 8-OHDPAT (for serotonergic) and dexamethasone (for PVH-HPA). The inhibitors may be used in low dosages.

Dipivalyl-6-fluoronorepinephrine (dp6FNE), a brain-permeable pro-drug of the synthetic catecholamine, 6FNE is the only existing α-adrenergic selective agonist that has full efficacy at both brain $α_1$- and $α_2$-adrenoceptors (Daly et al., *J. Pharmacol Exp. Ther*. (1980) 212: 382-389; Johnson et al., *European Journal of Pharmacology* (1986) 129: 293-305; Jurgens et al., *Molec. Pharmacol*. (2007), 71:1572-1581), both of which densely populate and potently inhibit the neural activity of the locus coeruleus (LC), one of the key stress areas of the CNS. (Stone et al., *Brain Research* (2009) 1291: 21-31) 6FNE demonstrates both potent and rapid antidepressant effects in mouse models of chronic depression when infused in the 4th ventricle in the vicinity of this nucleus. (Stone et al., *Neuropsychopharmacology* (2011) 14: 319-331) Catecholamines given peripherally cannot normally penetrate the blood brain barrier due to their polarity. However, the addition of lipophilic pivalyl groups permits these compounds to gain entry to the brain where they are enzymatically converted to back to the free catecholamines, which can then act upon membrane receptors. (Introini-Collison, et al., *Brain Res*. (1977) 572: 81-86). Peripheral administration of dp6FNE acutely inhibits LC neural activity and produces an immediate antidepressant effect in models that do not respond to acute treatments. A similar action occurs with the closely related pro-drug, dipivalyl-epinephrine (dpEPI), because its parent catecholamine, epinephrine (EPI), is also a full agonist at these two α-receptors. Johnson et al., *European Journal of Pharmacology* (1986) 129: 293-305) However, because EPI also stimulates β-adrenoceptors which may activate LC neurons, it may be necessary to first block β-receptors prior to its administration. (Nestler et al., *Biol Psychiatry* (1999) 46: 1131-1139)

We administered the pro-drugs shortly before one or more tests of antidepressant activity including reversal of immobility during tail suspension and forced swimming and attenuation of anhedonia produced by endotoxin administration. To preclude the activation of $α_1$-adrenoceptors in the cardiovascular system, the drugs were administered with a low dose of the $α_1$-antagonist, prazosin, 0.2 mg/kg, which is below the dose necessary for either penetration of the brain or alterations in behavioral activation in Swiss-Webster mice. (Stone et al., *Eur. J. Pharmacol*. (2001) 420: 97-102) Because dp6FNE like all other antidepressants has an initial anorexic effect and acutely reduces the consumption of sweet solutions, in the test for anhedonia it was necessary to employ a non-nutritive hedonic behavior, FUST (sniffing of estrous female urine). (Malkesman et al., *Biol. Psychiatry* (2010) 67: 864-871) The latter behavior like other hedonic activities is impaired by chronic stressors that induce behavioral depression and is rescued by chronic antidepressant treatment. To demonstrate that dp6FNE is more rapidly-acting than currently available drugs, its acute effects were compared with those of a panel of antidepressants on a variant of the forced swim test—the repeated forced swim (RFS) test —which has been shown to respond to repeated but not acute antidepressant administration. (Stone et al., *Neuropsychopharmacology* (2011) 14: 319-331); Sun et al., *J. Neurosci. Methods* (2003) 126:35-40; Sun et al., *Behavioral Pharmacology* (2008) 19: 334-338). To demonstrate which α-receptor mediates the actions of dp6FNE, the effects of selective antagonists on its effects were also assessed. Finally, to demonstrate any effects on locomotor activity, the drug was also tested on behavior in an open field.

The data provided demonstrate that dp6FNE/prazosin possesses antidepressant activity after systemic administration in mice using a variety of tests. The drug combination given i.p. reduced immobility in the TST and RFS tests, and also rescued a hedonic behavior, FUST, that was impaired by pretreatment with endotoxin. The RFS test responds to a much lower dose. This may be due to a greater level of stress caused by the TST than the RFS judging from the abilities of the two to activate Fos expression in the paraventricular hypothalamus. (Stone et al., *Neuropsychopharmacology* (2011) 14: 319-331) In addition, the lower doses are more effective on immobility than the higher doses. The loss of effect at higher doses may result from entry of the drug into and inhibition of non-stress brain regions, suggesting a greater selectivity of the lower doses for stress areas.

In the RFS, the anti-immobility action of dp6FNE was accompanied by an increased distance swum but this effect was observed only at the higher doses. This difference in sensitivity of the two behaviors to the drug may be due to the greater effort necessary for swimming behavior compared to use in smaller limb movements that terminate immobility. The effect of the drug on distance swum but not immobility fades significantly with chronic administration. The effect of the drug combination on the TST or RFS may not be due to prazosin since the antagonist, when tested alone at the dose of 0.2 mg/kg, did not affect these measures, although an interactive effect cannot be excluded. Furthermore, the antidepressant effect of dp6FNE may not be the result of a generalized increase in motor activity since no stimulant action was observed in the open field test which readily detected the activating effect of amphetamine.

Dp6FNE/prazosin has a significantly faster onset of action in the RFS than a panel of currently available antidepressants including DMI, fluoxetine, bupropion, ketamine and clonidine. The data demonstrate that the pro-drug was the only agent of this group that either significantly reduced immobility or increased distance swum within minutes of a single administration. The RFS test has been shown to respond to chronic but not acute administration of established antidepressants. There is also evidence that the endotoxin-anhedonia model, which was also reversed by acute dp6FNE/prazosin, also requires chronic antidepressant treatment. (Yirmiya et al., *Brain Res*. (1996) 711: 163-174) These data demonstrate that depressive behavior is maintained by ongoing hyperactivity or hyperresponsivity of central stress regions and can be immediately reduced by acute pharmacological inhibition of these. Although most antidepressant agents have been shown to produce long lasting changes in gene and protein expression, neurogenesis and synaptic morphology. (Marchetti et al., *Biol. Psychiatry* (2010) 67: 146-154; Schmidt et al., *Behavioral Pharmacology* (2007) 18: 391-418; Stone, *Behavior and Brain Sciences* (1983) 6: 535-578), these alterations may not be obligatory for the acute pharmacological inhibition of depressive behaviors but rather may be more involved in producing persistent biases in reactivity.

Dp6FNE was designed to stimulate inhibitory $\alpha_1$- and $\alpha_2$-adrenoceptors in or near the LC after systemic administration. The data support this action by showing that blockade of these receptors with either a high dose systemic prazosin or the $\alpha_2$-antagonist, atipamezole, significantly reversed the antidepressant actions of pro-drug in the RFS. Although both antagonists reverse the antidepressant effect, blockade of $\alpha_1$-receptors apparently affects baseline RFS behaviors to a greater extent since immobility and distance swum were affected more by high dose prazosin than atipamezole. This is consistent with the earlier finding that stimulation of $\alpha_1$-receptors in or near the mouse LC produces greater inhibitory actions on its neural activity as measured by Fos expression than of $\alpha_2$-receptors. (Stone et al., Brain Res. (2009b) 1291: 21-31) In further support, a second dipivalyl substituted catecholamine, dpEPI, which also has full agonist actions at $\alpha_1$- and $\alpha_2$-adrenoceptors, also produces a similar acute antidepressant action in the RFS. This demonstrates that this class of drugs produces extremely rapid antidepressant effects.

Although dp6FNE was designed to be a temporary treatment, the present data indicate that its anti-immobility effect at 0.5 mg/kg, i.p., persists for at least 11 daily treatments whereas its ability to increase swimming distance may fade and become insignificant at this time. Therefore, there may be a desensitization of the responsible adrenoceptor(s). Although no formal measures were employed, no obvious signs of toxicity in terms of reduced arousal or disheveled fur coat were observed after repeated treatment.

Example 1 dp6FNE and the LC dp6FNE, at or below 3 mg/kg i.p., can selectively reduce Fos expression in the LC compared to the PVH during the RFS model and also preferentially inhibit the LC in the tail suspension test (TST) which is more stressful. In the RFS study, mice were subjected to 4 daily 15 min swims as described above and were injected i.p. with either vehicle or dp6FNE (3 mg/kg) 15 min prior to the 5th swim. In the TST study, animals were injected similarly before a 6 min test. Both the vehicle and drug solutions contained a low behaviorally-inactive dose of prazosin (0.2 mg/kg) in order to block peripheral $\alpha_1$-adrenoceptors from stimulation by liberated 6FNE. Prazosin at this dose does not penetrate the blood brain barrier in mice or have effects on exploratory behavior (Stone et al., Eur J. Pharmacol (2001) 420: 97-102). The animals were anesthetized and perfused for immuno-histochemistry 70 min after the start of the swim or tail suspension. Brains were processed as described previously for double-label immunofluorescent Fos/tyrosine hydroxylase staining of all sections through the LC and for single-label Fos staining through the full PVH (Stone et al., Brain Res (2009) 1291: 21-31). Both nuclei were counted in their entirety for Fos/TH (LC)- and Fos-only (PVH)-containing neurons by ImageJ. dp6FNE in the swum animals produced a 33.6±6.8 reduction in gene expression in the LC and a 13.0±20.1% reduction in the PVH. In the tail suspended mice the analogous reductions were 53.5±7.2% (LC) and 36.7±3.1 (PVH). Comparison of vehicle animals with previous results without prazosin indicated no effect of the antagonist on LC or PVH Fos at this dose (Stone et al., Brain Res (2009) 1291: 21-31); Stone et al., Progress in Neuropsychopharmacology and Biological Psychiatry (2007) 31: 1195-1207; Stone et al., Eurs J Pharmacol (2007) In press). These findings thus indicate that a dose of oral dp6FNE that has preferential inhibitory effects on the LC during depression exists.

Example 2

Dexamethasone and the PVH

GR agonists such as corticosterone and dexamethasone are well known to produce selective inhibition of the neural activity of parvocellular PVH neurons at low doses (Keller-Wood et al., Endo Rev (1982) 5: 1-24; Dallman et al., Ann N Y Acad Sci 91987) 512: 402-414). This effect was shown in a previous experiment on the effects of corticosterone in the drinking water on Fos expression in the PVH or piriform cortex of mice subjected to the RFS model (Stone et al., eur J Pharmacol (2007) In Press). The animals were swum a total of 3 times and on the night prior to the 3rd swim given corticosterone at 12.5, 25 or 50 µg/ml in the drinking water. These concentrations produced nighttime intakes of 4.6, 10.7 and 14.2 mg/kg. The mice were given the 3rd and final swim the following morning, 0800-1000 h, and were anesthetized and perfused 70 min after the start of the swim for immunohistochemical assay of Fos in the PVH and in the piriform cortex, a control region that supports positively motivated behavior (Carr et al., Neuropsychopharmacology (2010) 35: 752-763; Stone et al., Neurosci Biobehav Revs (2008a) 32: 508-524). The previous night's corticosterone treatment significantly inhibited PVH Fos expression at all 3 doses on the following morning producing reductions of −51.7±17, −66.8±8.5 and −63.7±11.0%, (all p's<0.05 versus veh) and to significantly increase expression of the gene in the piriform cortex (+203.3±78.6, +175.3±53.9, +193.3±67.4%, all p's<0.05 versus veh). These findings confirm that GR agonists have highly selective and persistent inhibitory actions on the PVH with opposite actions on "positive" structures, and that a similar selective low oral dose for the more GR-selective agonist, dexamethasone, may be provided.

Example 3

The "Cocktail" and LC, PVH, and Raphe

Subjects: Swiss Webster male mice, 8-10 weeks of age, are used. The mice are housed singly, to preclude fighting, with nesting material under a 12:12 h dark:light schedule (on 5 AM) at 22±1° C. for one week prior to all experimental procedures. Food and water is made available ad libitum.

Procedure:

Mice are subjected to 4 daily 15 min swims (0800-1200 h) in tepid water (32-34° C.) in rat tub cages (24×43×23 cm w×h×l) on 4 successive days to induce a model of chronic depression and animals showing at least 5 min immobility on the 4th swim selected for the experiment [65-75% of the total population (Stone et al., Neuroscience (2010) In press). Forty-five min prior to the 5th and last swim the selected animals are given orally one of the following drugs at the following doses (all in mg/kg): dp6FNE (veh, 0.1, 0.3, 1, 3); dexamethasone sodium phosphate (veh, 0.01, 0.03, 0.1); 8-OHDPAT (veh, 0.01, 0.05, 0.1). The dose range for dp6FNE is based on the above preliminary' study while that for dexamethasone is based on the above corticosterone study assuming a dosage equivalence of 1/30 between the two corticosteroids (McAuley, Corticosteroid conversion website (2010) and a bioavailability of approximately 0.5 for oral dexamethasone sodium phosphate (Hare et al., Clin Pharmacol Ther (1975) 18: 330-337). The highest dose of dexamethasone that can be used is 1/10 of that reported to cause either hypertension (Bernal-Mizrachi et al., *Cell Metabolism* (2007) 5:91-102; Goodwin et al., *Biochemical and Biophysical Research Communicaitons* (2010) 394: 266-271) or insulin resistance in mice (Ghaisas et al., *J Ethnopharmacol* (2009) 122: 304-307). All solutions also contain a low dose of prazosin (0.2 mg/kg). To control for the remote possibility that this dose can alter central Fos expression, two additional groups that receive the vehicle and dp6FNE (0.3 mg/kg) without the antagonist are included.

70 Min after the start of the swim all mice are anesthetized with isoflurane (1-2%) followed by urethane (2.2 g/kg) and perfused with 25 ml saline followed by 100 ml of 4% paraformaldehyde. Tissues are processed for immunohistochemistry as previously described (Stone et al., *Brain Res* (2009) 1291: 21-31). In brief, after sucrose infiltration, the brains are sectioned frozen at 35µ and all sections comprising the entire rostral-caudal extents of the 3 stress regions—LC, PVH and raphe system—along with every 5th section from the following "positive" areas [secondary motor cortex (M2), piriform cortex (Pin), anterior nucleus accumbens (NAC), lateral septal nucleus (LS)] are saved and stained for the appropriate antigens. Two additional stress-sensitive regions, the bed nucleus of the stria terminalis (BNST) and the medial nucleus of the amygdala (amyg) are saved for possible contingent use (see below). The LC, PVH, raphe nuclei (dorsal and median) are double-labeled for Fos in the presence of the following region-specific antigens: tyrosine hydroxlase (LC), corticotrophin releasing factor (PVH) or 5HT (raphe nuclei) respectively using immunofluorescent procedures described in our previous publications (Stone et al., *Brain Res* (2009) 1291: 21-31). The BNST, amyg, M2, Piri, NAC and LS are single labeled for Fos using colorimetric methods (nickel intensified DAB) with alternate sections stained with cresyl violet to aid anatomical localization.

In the stress areas, the entire structure in every section is counted manually, assisted by ImageJ, for the number of Fos-positive, antigen-positive (TH, CRF, 5HT), and double labeled cells (thresholding at 2.5× background fluorescence) and the proportion of antigen-positive cells expressing Fos computed. In the single labeled regions, Fos-positive cells are counted automatically by ImageJ in structures outlined from atlas dimensions (Franklin et al., *The Mouse Brain in stereotaxic Coordinates* (1997) and expressed per unit volume. Because the applicants are interested only in relative changes in the present experiments, a profile cell-counting method which has been modified to avoid placement bias by the counting of every positive cell in the structure of interest in each section is employed. This method is significantly less time consuming than stereological procedures. No correction for double counting of cells is made because of the relatively thick sections used.

Data Analysis, Expected Results, Interpretation and Alternate Plans:

The minimum effective dose for inhibition of a stress region is defined as the lowest dose that produces a significant decrease in Fos expression in its targeted region compared to the vehicle group (assuming there is no difference between the prazosin and non-prazosin vehicles) without causing a similar decrease in any of the "positive" areas during the forced swim stress. For this analysis the various doses for each drug are compared with the vehicle with separate one-way ANOVAs and the significance of the difference of each dose group from the vehicle group estimated with a conservative multiple comparisons test (Neuman Keuls) to insure that the difference is robust.

Figure 3:
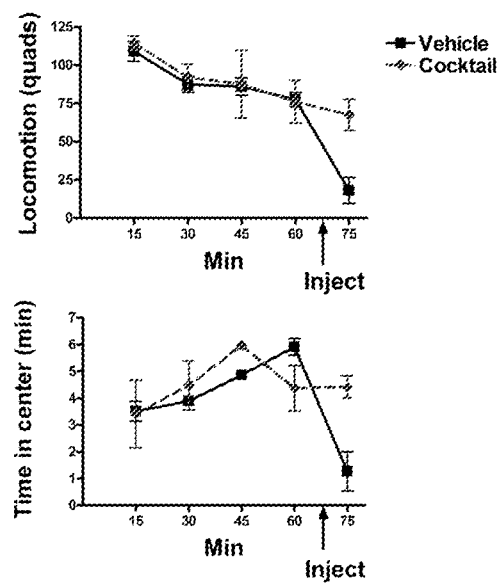
FIG. 3 depicts an anxiolytic effects of "cocktail" of dp6FNE (1), 8OHDPAT (0.05) and corticosterone (3 mg/kg) i.p. on open field behavior (locomotion and center square occupancy) and absence of sedative or stimulant actions. The mixture, injected at arrow, rescued the reductions in activity and center square time caused by the capture and injection procedure (N=3).

Preliminary results on the effects of both corticosterone in the PVH versus the *Piri* cortex, and dp6FNE in the LC versus the PVH, along with previous findings by others on effects of 8-OHDPAT on raphe neural activity (Maier et al., *Behav Neurosci* (1995) 109: 404-412; Nalivaiko et al., *Am J Physiol Regul Integr Comp Physiol* (2005) 289: R596-R604) as well as the anxiolytic effect of the mixture of all 3 agonists (FIG. 3) suggest that it is feasible to obtain relatively selective inhibitory doses of these compounds for these stress areas. This is further supported by the higher sensitivities of the autoreceptors involved in these negative feedback effects than postsynaptic receptors Adler et al., *J Pharmacol Exp Ther* (1987) 240: 508-515; Spear, et al., *Eur J Pharmacol* (1991) 203: 9-15).

Example 4

Antidepressant and Anxiolytic Effects of dp6FNE, 8-OHDPAT and Dexamethasone

This experiment tests the putative antidepressant actions of each of the above 3 agonists and their combination on acute tests involving both motoric (RFS-immobility) and hedonic (CMS-anhedonia) behavioral endpoints and determines whether the "cocktail" is superior in acute efficacy to currently available antidepressant agents and electroshock therapy. Motor activity is controlled for in open field tests while anxiety is assessed both in the open field and in a plus maze to determine the specificity of the above effects for depressive behavior.

Preliminary Data:

The following preliminary experiments suggest that systemic dp6FNE has significant acute antidepressant effects in both the immobility-based RFS and hedonic-based endotoxin-anhedonia models as well as a significant anti-anxiety effect in the open field test, and that these effects are not confounded by changes in motor activity or sedation. Furthermore, comparison with other antidepressants in the RFS test, suggests that the compound is more effective or rapidly acting than other currently available antidepressants including ketamine. In addition, the antidepressant effects of dp6FNE were increased by co-administration of low doses of 8-OHDPAT and corticosterone. Although the small N's used in most of these studies (3/group) precluded statistical analyses, projections indicated that significance would be achieved for these effects with N's of sufficient power.

Example 4a dp6FNE & RFS-Immobility

Figure 4:
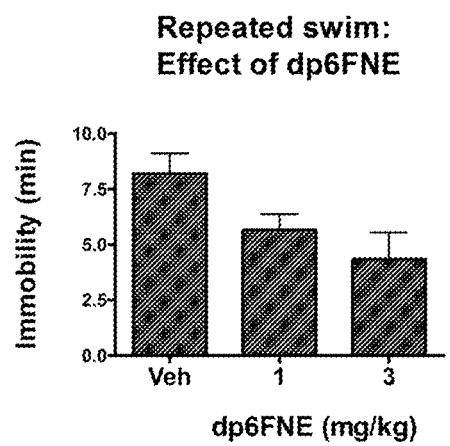
FIG. 4 depicts dose dependent reduction of immobility in RFS model by acute i.p. dp6FNE, 15 mm prior to swim.
Figure 5:
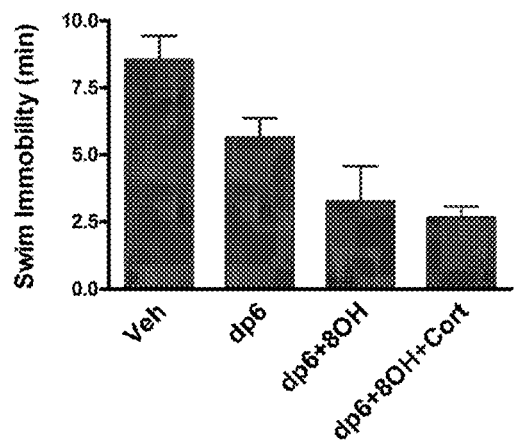
FIG. 5 demonstrates the effect of co-administration of low i.p. doses of 8OHDPAT (0.05 mg/kg) and corticosterone (3 mg/kg) on anti-immobility effect of i.p. dp6FNE (1 mg/kg) in RFS test. Note progressive enhancement of antidepressant effect as raphe and PVH-HPA stress systems are inhibited along with LC (N=3)

Mice were swum for 15 min/d on 4 d and tested for the response to acute i.p dp6FNE (1 or 3 mg/kg) alone or in combination with 8-OHDPAT (0.05 mg/kg) and corticosterone (3 mg/kg) on the 5th and final swim (15 min after drug administration). All solutions contained 0.2 mg/kg prazosin. Comparison groups receiving currently available antidepressants were treated acutely i.p. or chronically (14 d osmotic pumps) with either desmethylimipramine (DMI) (10 mg/kg), fluoxetine (5 mg/kg), escitalopram (5 mg/kg), bupropion (10 mg/kg) or ketamine (10 mg/kg). Immobility (floating) and distance swum were measured from videorecordings as described previously (Stone et al., 2008b). dp6FNE produced a dose-dependent decrease of immobility having a maximum effect of $-39.4 \pm 16.6\%$ at 3 mg/kg (FIG. 4) and an increase of distance swum of $+77.5 \pm 5.2\%$ at 1 mg/kg (not shown). None of the currently available antidepressants that were tested, including ketamine, appeared acutely effective on this test, although when given chronically (14 d) most had marked effects (FIG. 1). Successive additions of low doses of 8-OHD-PAT and corticosterone to dp6FNE produced further progressive decreases in immobility culminating in a maximal reduction of −68.9±5.9% (FIG. 5) and a maximal increase of distance swum of +112.3±10.1% above vehicle levels (not shown). The correlation between the number of agonists coadministered and immobility was −0.83, df=4, p<0.05 whereas for distance swum it was +0.68, df=4, p=0.13 (not shown).

Figure 6:
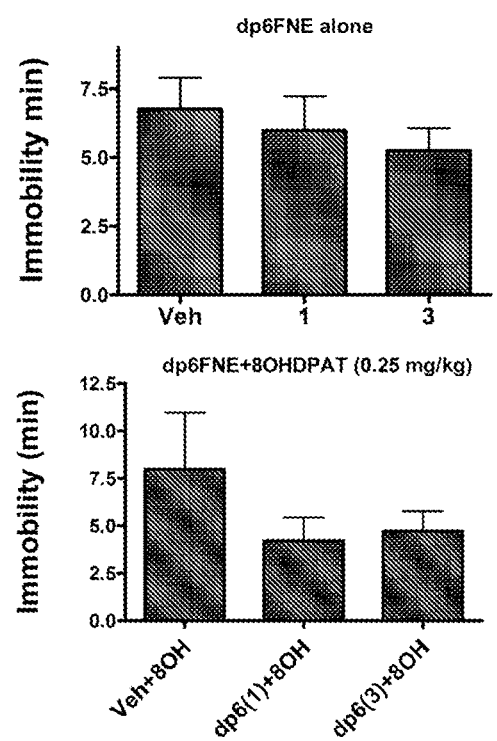
FIG. 6 demonstrates the effectiveness of oral dp6FNE alone and with 8OHDPAT (+45 min) on immobility in RFS test. Results suggest adequate absorption from GI tract with sufficient bioavailability and brain penetration of both compounds (N=3-4).

To determine if similar effects would be obtained with oral administration, mice were tube fed dp6FNE (with 0.2 mg/kg prazosin) in the absence or presence of 8-OHDPAT (0.25 mg/kg) 45 min prior to the 5th swim (FIG. 6). The pro-drug again produced a dose-dependent reduction in immobility which was enhanced by 8-OHDPAT co-administration to reach a maximum of −43.7±15.6% and a dose-dependent increase in distance swum with 8-OHDPAT of +76.4±42.4% of vehicle levels.

Example 4b dp6FNE & LPS-Anhedonia

To determine if dp6FNE would also be active in an anhedonia-based model of depression, the compound was tested for its ability to reverse an endotoxin-induced inhibition of the female urine sniffing test (FUST), a non-nutritive hedonic behavior, whose impairment by stress was recently validated as a model of depression in this species (Malkesman et al., *Biol Psychiatry* (2010) 67: 864-871) A non-nutritive rewarding behavior was used because dp6FNE, like most other acutely administered antidepressants, has initial anorexic effects that inhibit the consumption of sweet solutions (Currie et al., *Brain Res* (1998) 800: 62-68). Endotoxin was used as the depression-inducing agent rather than the more well-accepted chronic mild stress (CMS) model because it has been established that cytokine release is a key factor in mediating the depressive effects of stress (Anisman, *J Psych Neurosci* (2009) 34:4-20) and because the endotoxin model is significantly briefer (24 h versus 3-4 weeks) but yields largely the same information as the CMS model. The repeated forced swim (RFS) model could not be used for this test because it is not a severe enough stress to reliably produce anhedonia in this species (Stone et al., *Pharmacol Biochem Behav* (2008b) 91: 190-195).

Figure 7:
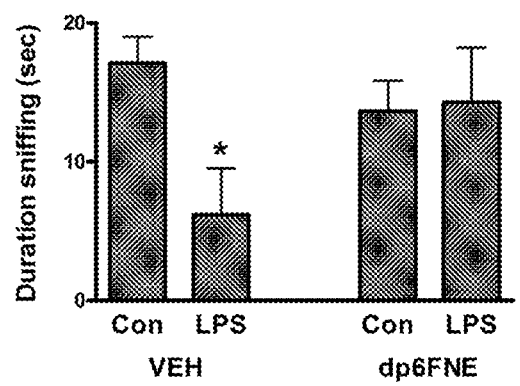
FIG. 7 demonstrates the reversal of endotoxin (LPS) inhibition of rewarding FUST behavior (anhedonia) by acute i.p. dp6FNE (1 mg/kg) (N=3-11) *p<0.05 versus Con.

Male mice were trained to sniff estrous urine (verified by vaginal smears) presented on cotton swabs in the home cage over 3 d and were matched on sniffing duration (proximity to the swab in a 3 min test) into control and depression groups. These groups were administered i.p. control solution ($H_2O$) or lipopolysaccharide (LPS), 400 μg/kg, respectively, and were left undisturbed for 24 h, which is necessary for the initial sickness behavior, but not the anhedonia, to subside (Frenois et al., *Psychoneuroendocrinology* (2007) 32: 516-531). The two groups were then further subdivided into matched vehicle and dp6FNE groups (with prazosin 0.2 mg/kg) and were tested for FUST behavior 15 min after receiving the respective i.p. injections. Results are shown in FIG. 7. Animals receiving vehicle showed a −63.7±19.4% reduction of time sniffing due to the prior endotoxin (Con vs LPS, $F_{1,23}$=6.97, p=0.01) whereas mice injected with dp6FNE had no reduction (+4.6±1.4%, Con vs LPS) indicating substantial and significant rescue of the behavior (LPS× dp6FNE interaction, $F_{1,23}$=2.91, p=0.10). Furthermore, the group receiving LPS+dp6FNE was no longer significantly different from the untreated control group, Con+ Veh ($F_{1,23}$=0.53, NS). In the absence of endotoxin, dp6FNE did not significantly affect the FUST ($F_{1,23}$=0.47, NS).

Figure 8:
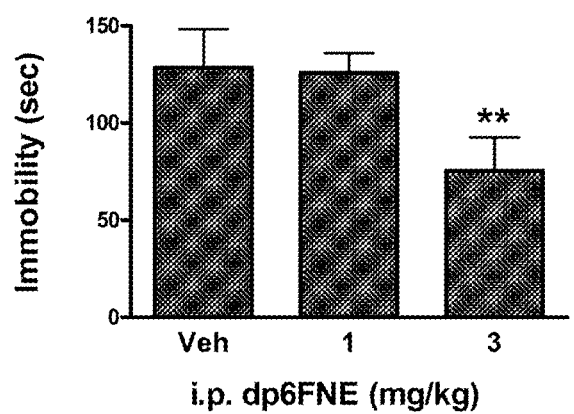
FIG. 8 demonstrates the effect of i.p. dp6FNE on immobility in tail suspension test. **p=0.01 versus Veh.

To determine if dp6FNE was active in a more traditional test of antidepressant activity, it was given as above 15 min prior to a tail suspension test. A significant reduction of immobility was found at the 3 mg/kg dose (FIG. 8, $F_{1,26}$=7.54, p=0.01, N=5-11).

Example 4c

"Cocktail" & Open Field Motor Activity and Anxiety

Figure 9:
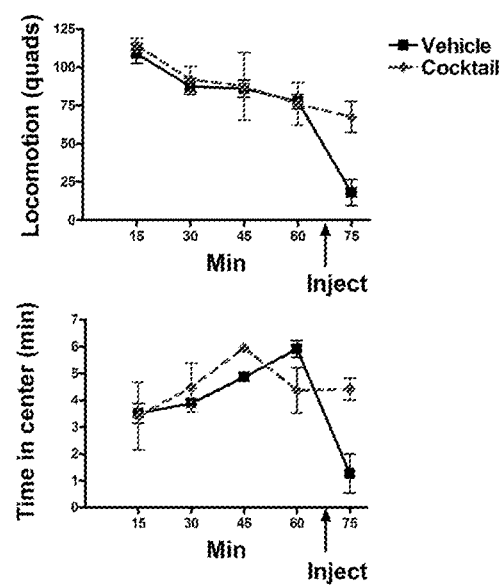
FIG. 9 demonstrates the anxiolytic effects of "cocktail" of dp6FNE (1), 8OHDPAT (0.05) and corticosterone (3 mg/kg) i.p. on open field behavior (locomotion and center square occupancy) and absence of sedative or stimulant actions. The mixture, injected at arrow, rescued the reductions in activity and center square time caused by the capture and injection procedure (N=3).

To determine if the agonists had motor stimulating or sedative actions, mice were allowed to explore an open field undisturbed for 60 min and were then captured and injected i.p. with either vehicle or the full "cocktail" of the 3 inhibitors (dp6FNE 1 mg/kg; 8-OHDPAT, 0.05 mg/kg; corticosterone, 3 mg/kg, praz, 0.2 mg/kg) before being replaced in the field for a final 15 min. The vehicle injection (praz present) reduced subsequent locomotion and time spent in the center of the field by −76.8±11.0% and −78.5±12.4%, respectively, from preceding levels, indicating an anxiogenic effect of the injection procedure. The injection of the "cocktail", however, rescued both locomotion and center time to −12.9±1.9% and −25.3±6.9%, respectively, indicating a strong anti-anxiety effect with no motor stimulation or sedation (FIG. 9). This finding suggests that it is possible to find minimally effective doses of these agonists that inhibit stress regions without inhibiting non-stress areas.

Example 4d

Corticosterone & RFS

Figure 10:
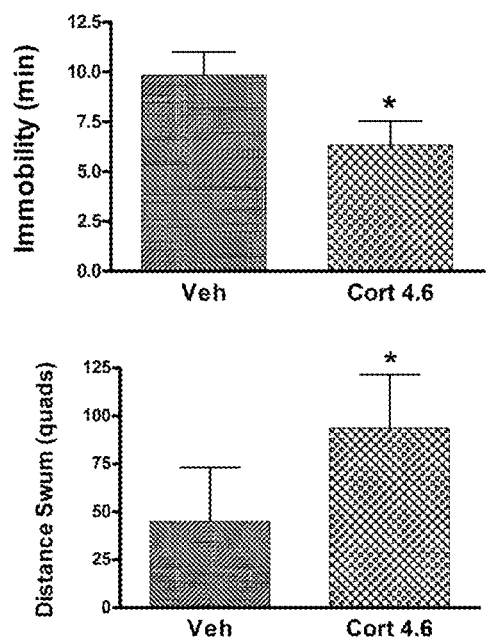
FIG. 10 demonstrates the anti-immobility effect of low dose of corticosterone (4.6 mg/kg) in RFS model. *p<0.05 v Veh.

Although corticosteroids are well known to produce depression (Gourley et al., *Biol Psychiatry* (2008) 64: 884-890), this occurs at high doses only. At low doses, (Stone et al., *Eur J Pharmacol* (2007); Zhao et al., *Brain Res* (2009) 1261: 83-90) have shown that the hormone produces significant antidepressant effects in both the RFS and Porsolt acute forced swim models. The results for the RFS model are shown in FIG. 10. Mice were swum for 3 d and given either vehicle (0.8% ethanol) or corticosterone (12.5 μg/ml) in their drinking water. This concentration produces a nighttime intake of 4.6 mg/kg. The hormone produced a significant reduction in immobility (−36.6±5.7%, $t_{10}$=2.36, p<0.05) and significant increase of distance swum (+107.7±15.8%, $t_{10}$=2.91, p<0.01). No effect was observed on open field locomotion.

Example 4e

Cocktail & RFS-Immobility

Figure 11:
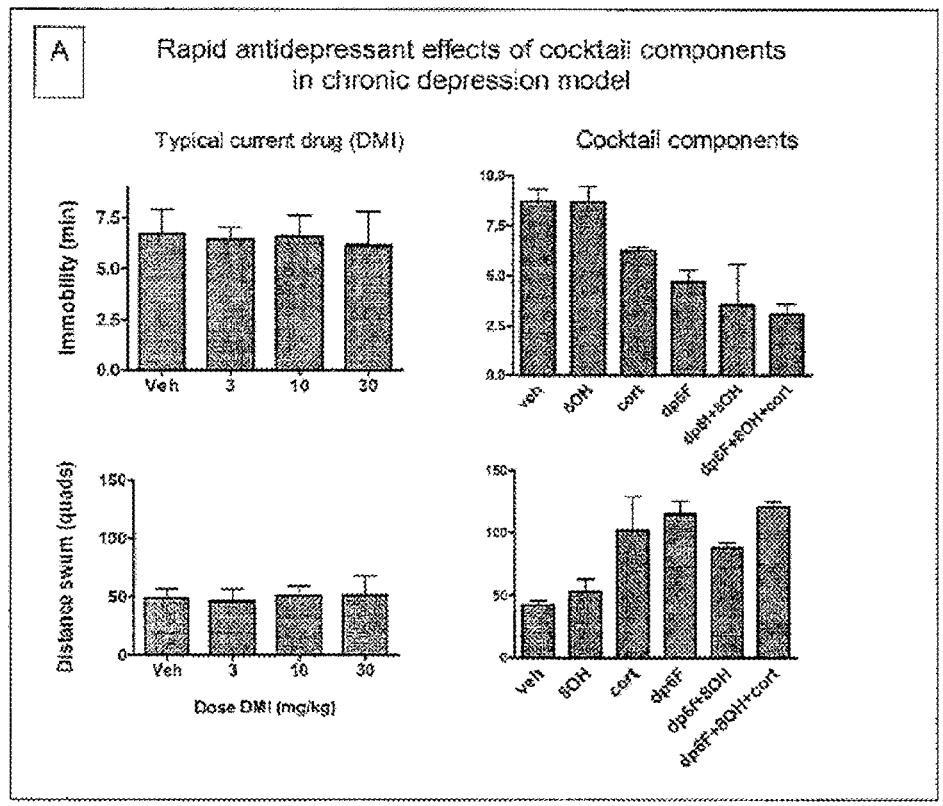
FIG. 11 shows the rapid antidepressant effects of the 3 anti-stress components of the cocktail (dp6FNE, 8-OHDPAT and corticosterone) in a mouse model of chronic depression (RFS) known to be resistant to acute antidepressant treatment. The effects of the components were additive and could be combined into a cocktail, N=5-8 mice per group.
Figure 11:
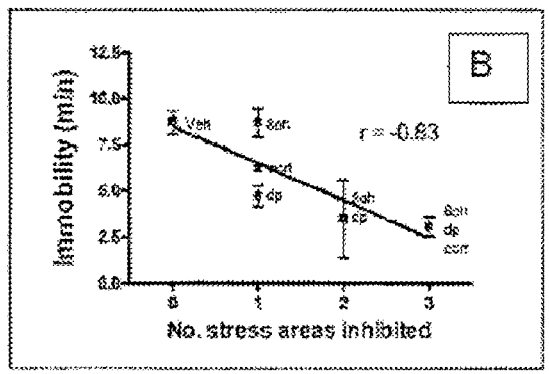
Figure 11:
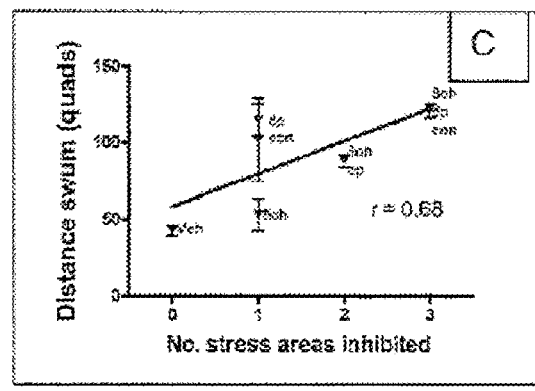

As described in Example 4a, the cocktail was tested in a mouse model of chronic depression (RFS). The applicants found that when given ip in low doses each of the above agonists (dp6FNE, 8-OHDPAT, and corticosteroid), produces an immediate and effective antidepressant action in this model (FIG. 11A). Furthermore, the effects of the individual compounds are additive so that they can be combined into a cocktail, that is much more effective than a standard antidepressant, desmethylimipramine (DMI) given acutely (FIG. 11A-C). The mixture also contains a low behaviorally-inactive dose of the alpha-1 antagonist, prazosin (0.2 mg/kg), in order to block the stimulation of peripheral cardiovascular alpha-1 adrenergic receptors by 6FNE. This dose of prazosin has not been found to affect the RFS model.

Figure 12:
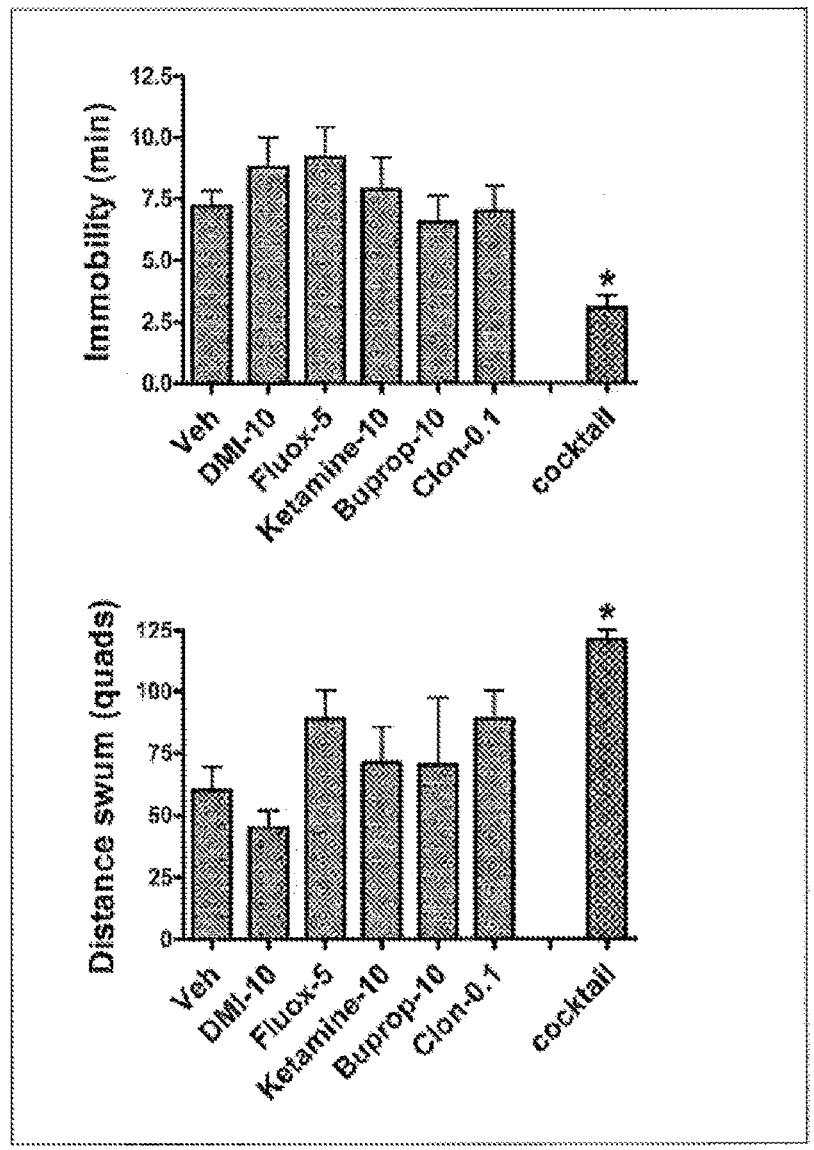
FIG. 12 shows the cocktail to be the only medication immediately effective in the chronic depression model compared to a panel of available antidepressants including desmethylimipramine (DMI) fluoxetine (fluox), bupropion (buprop), ketamine and clonidine (don). N=8-10. * P<0.05 versus vehicle.

In a further test, the 3-agonist cocktail was compared to a panel of currently available antidepressants including desmethylimipramine (DMI), fluoxetine, bupropion, clonidine and even ketamine, reputed to be the fast-acting currently available antidepressant and have found that the cocktail is the only medication producing a significant antidepressant effect minutes after a single administration (FIG. 12).

Figure 13:
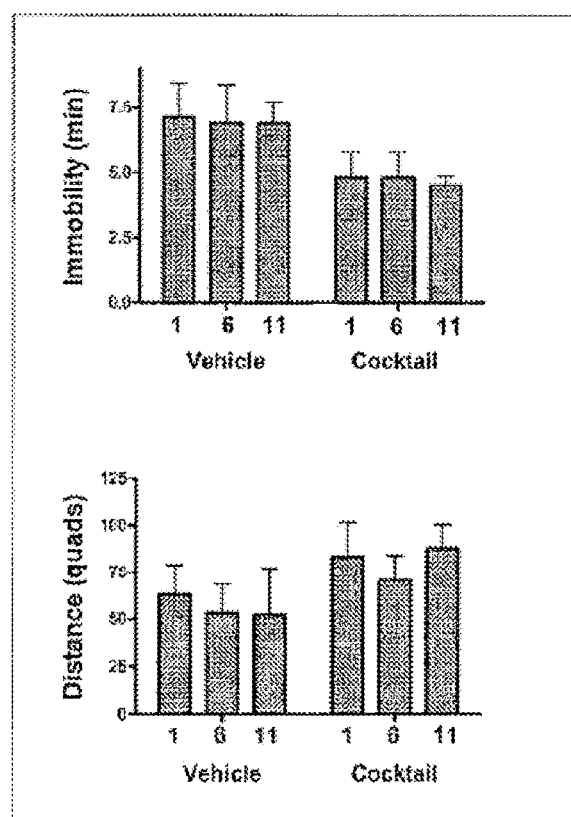
FIG. 13 shows the maintenance of the antidepressant effect of the cocktail in the chronic depression model when administered repeated over the course of 11 days. N=5-7.

To determine if the cocktail retained its antidepressant effects when adminstered repeatedly, mice, previously subjected to the RFS procedure, were injected daily with the cocktail for 11 consecutive days and assessed for depression from swims after the $1^{st}$, 6th, and 11th injections. The results shown in FIG. 13 indicate that the antidepressant effects on both immobility and distance swum are maintained over this interval.

In addition to its antidepressant property, the cocktail is also effective in producing a significant antianxiety effect without sedation in these animals. The applicants have tested for this effect using an open field in which animals are placed and permitted to explore freely after which they are captured, restrained briefly for an ip. injection of saline and returned to the field for a final 15 min. The level of anxiety is inferred from the inhibition of motor activity and reluctance of the animals to enter the center portion of the field after the capture and injection. The handling and saline injection procedure markedly reduces subsequent locomotion and time in the center of the field, consistent with an anxiogenic effect, while the cocktail completely prevents both effects indicating a strong anti-anxiety action (FIG. 9).

Furthermore, the cocktail does not increase or decrease general locomotor activity compared to the pre-injection levels indicating that it does not produce either sedation or a nonspecific increase in motor activity.

Example 5a

Progressive Inhibition of Stress Circuit and Antidepressant Effect

The proposed experiment replicates the effects of dp6FNE, 8-OHDPAT and a corticosteroid both individually and together on both an immobility-based and an anhedonia-based model of depression. The corticosteroid can be changed to low-dose dexamethasone since this is a more selective GR agonist than corticosterone. The immobility model is used is the RFS as above while the anhedonia model can be changed to chronic mild stress (CMS) as this is a more established method than the LPS procedure used in the pilot research. Although the RFS model has only recently been developed, it has been validated by demonstrations of its responsiveness to chronic IMI, DMI, escitalopram, fluoxetine, mianserin, alaprocate, tranylcypromine and iproniazid and its lack of responsiveness to the non-antidepressants, diazepam, haloperidol and buspirone (Sun et al., *J Neurosci Methods* (2003) 126: 35-40; Sun et al., *J Pharmacol Exp* (2005) 52:90-110); Stone et al., *Current Protocols in Neuroscience* (2010) In press). It is necessary to employ both models because the CMS procedure, although effective for anhedonia, cannot be used to reliably induce immobility during swims because it has been shown several times to elicit increased swimming/struggling behavior under certain conditions (Haidkind et al., *Eur Neuropsychopharmacol* (2003) 13:19-28; Harro et al., *J Neural Transm* (1999) 106: 619-629).

The Protocol:

Mice are subjected to either non-stress control conditions (handling twice weekly) or to one of the above two depression models, RFS for 4 d or CMS for 3 weeks. The procedure for the RFS has already been described in detail above. The CMS model entails the application of a random series of twice-daily stressors including 12 h periods of food or water deprivation, 15 min of forced swim in 25° C. water (15 min), soiled cages (overnight), tilted cages (overnight), lights on (dark cycle), repeated 24 h grouping with unfamiliar cagemates, and 60 min of restraint stress as per Willner et al (Willner, *Neuropsychobiology* (2005) 52: 90-110). Depression is assessed from the reduction of sniffing time of female urine (FUST, female urine sniffing test), tested at weekly intervals for 3 weeks. (Animals subjected to this procedure are monitored for changes in daily food intake and removed from the study if this falls more than 25% from baseline.) The FUST test has now been shown to be reduced by cytokine release (FIG. 7) and the learned helplessness model of depression in mice and to respond to chronic antidepressant therapy (Malkesman et al., *Biol Psychiatry* (2010) 67: 864-871). During the induction periods for both the RFS and CMS models, all mice are habituated 3× to oral tube feeding of tap water (0.2 ml).

Once the depression behaviors have developed, animals showing significant degrees of impairment in their respective behavioral endpoints [≥5 min of immobility in the RFS test and ≥30% reduction of sniffing in the FUST test which on the basis of the applicants' previous research may occur in approximately 65-75% of all subjects (Stone et al., *Current Protocols in Neuroscience* (2010) In press)] are matched on the depressive behaviors into 5 groups that received respectively oral dp6FNE, 8-OHDPAT, dexamethasone, full "cocktail" (dp6FNE+8-OHDPAT+dexamethasone) or vehicle in tap water containing 0.2 mg/kg prazosin. To control for the effects of prazosin 2 additional groups that receive water and dp6FNE without the latter drug are included. The drugs are administered orally 45 min in 0.2 ml of tap water vehicle prior to the above antidepressant tests and at the minimum effective dosages to inhibit stress regions found in the preceding phase of the project. Depression can be assessed in blind fashion as described above. Because of the large number of groups and animals involved the study can be run as a series of replications each with 2-3 animals per group.

Data analysis progressive experiment: All behavioral variables are tested initially for homogeneity of variance and normality (Zhang, Am Meet Amer Educ Res Assoc (1998)), and, if necessary, transformed by conversion to either logs or square roots prior to ANOVAs. Each behavioral measure is then analyzed by a separate one way ANOVA followed by Bonferroni-corrected planned comparisons between each of the single drug groups (dp6FNE, 8-OHDPAT, dexamethasone) and the vehicle (assuming no difference between the vehicles with and without 0.2 mg/kg prazosin), and between the "cocktail" group and each of the single drug groups. In addition, linear regression coefficients are computed for each depression score as a function of the reduction of the Fos responses in each of the stress nuclei and for the average reduction of all 3 nuclei, found in the previous phase both in terms of absolute numbers of Fos-positive neurons and in terms of percent reductions from the vehicle control. If the "cocktail" group shows significantly lower depressive scores than each of the single drug groups, and if each of the single drug groups also have significantly lower scores than the vehicle group, then it can be concluded that the hypothesis is supported that antidepressant action is a direct function of the degree of inhibition of the stress system. This would be further tested by calculating the significance of the regression coefficients between the degrees of antidepressant effect achieved as functions of the reductions of Fos-expression in each of the stress nuclei or of the average reduction of all 3.

In the event of likely positive results (see FIG. 5), further experiments may be undertaken to determine if the effects of the agonists are due to non-specific motor stimulation, to what extent the actions of the agonists are selective to depression or also treat anxiety, and whether the acute effects of the agonist are transient or persistent. Effects on motor activity will be examined by oral administration of the "cocktail" or vehicle to both non-stressed and RFS-stressed mice 45 min prior to a videotaped 75 min open field test. Locomotion and rearing responses will be measured by a combination of videotracking and manual counting. A measure or anxiety will be obtained in this same experiment from the time the animals spend in the center of the field both before and after being picked up at 60 min (Ramos et al., *Behav Brain Res* (1997) 85: 57-69). A second measure of anxiety will be obtained with similar treatment groups in the elevated plus maze by standard open arm/closed arm entries and occupancies (Pellow et al., *J Neurosci Methods* (1985) 14: 149-167). To determine if effects are transient or persistent, mice will be subjected to the above two depression models and administered the agonist "cocktail" as above but the animals would be tested for antidepressant effects after delays of 24 and 48 hr.

Example 5b

Comparison with Currently Available Antidepressants

To compare the effectiveness of the new medication on depression with established antidepressants, a second experiment may be conducted comparing the "cocktail" with 6 currently available drugs (DMI, escitalopram, fluoxetine, reboxetine, tranylcypromine, and ketamine) and one non-pharmacological antidepressant treatment (electroshock, ECS) given acutely.

Protocol: Animals subjected to one or the other of the above depression models along with non-stressed controls will receive a single oral administration of either vehicle, DMI 10, escitalopram 5, fluoxetine 5, reboxetine 10, tranylcypromine 10, ketamine 10 mg/kg, or the agonist "cocktail" (with praz 0.2 mg/kg) 45 min prior to the 5th swim (RFS model) or the final FUST test (CMS model). Mice receiving ECS will be shocked through ear clip electrodes at 100 pulses/s, 55 mA, duration 0.5 s 2 h prior to these tests (Newton et al., *Eur J Neurosci* (2006) 24: 819-828).

For analysis, separate one way ANOVAs would be run on each of the behavioral variables for the 9 groups (8 antidepressant+cocktail groups) involved followed by planned Bonferroni-corrected comparisons between the "cocktail" group and each of the established drug and ECS groups to determine if the acute "cocktail" is significantly more effective than the acute established antidepressants on these two chronic depression models.

More information on the catecholamine, 6-fluoronorepinephrine, and its prodrug dipivalyl-6-fluoronorepinephrine (dp6FNE, Compound of formula IIIc) is given below.

The synthetic catecholamine, 6-fluoronorepinephrine 6FNE, is a potential new antidepressant that may be capable of overcoming some of the difficulties associated with antidepressant agents, particularly therapeutic lag time. In previous unrelated studies with this compound (Stone, et al., *Brain Res* (2009) 1291: 21-31; Stone, et al., *International Journal of Neuropsychopharmacology* (2011)), it unexpectedly produced several signs suggestive of rapid antidepressant and anti-stress activity after injection into the ventricular system of the brain. These included an immediate inhibition of brain circuits involved in stress and a disinhibition of circuits involved in motivated behavior leading to enhanced behavioral performance. The inhibited stress-sensitive nuclei included the locus coeruleus (LC), where the drug appears to principally act, and the paraventricular nucleus of the hypothalamus (PVH). However, 6FNE is a polar compound which does not pass the blood brain barrier and therefore cannot be administered systemically. To overcome this problem, the antidepressant properties of peripheral administration of a lipid-soluble pro-drug derivative of it, dipivalyl-6FNE (dp6FNE), that does pass the blood brain barrier and is enzymatically cleaved within the brain to yield the active parent catecholamine, 6FNE (Introini-Collison, et al., *Brain Res* 1992; 572: 81-86; Wang; et al., *J Pharmacol Exp Ther* 1977; 203: 442-448) was tested. The new drug was given along with phentolamine (5 mg/kg, i.p.), an α-antagonist that does not enter the brain (Anden, et al., *Psychopharmacology* 1974; 38: 91-103), because peripheral α-adrenoceptors, unlike their central counterparts, have pro-depressive and anxiogenic actions (Harsing, et al, *Pharmacology Biochemistry and Behavior*, 1989; 32: 927-932; Wong, et al., *Proc Natl Acad Sci USA* 2000; 97: 325-330).

Figure 14:
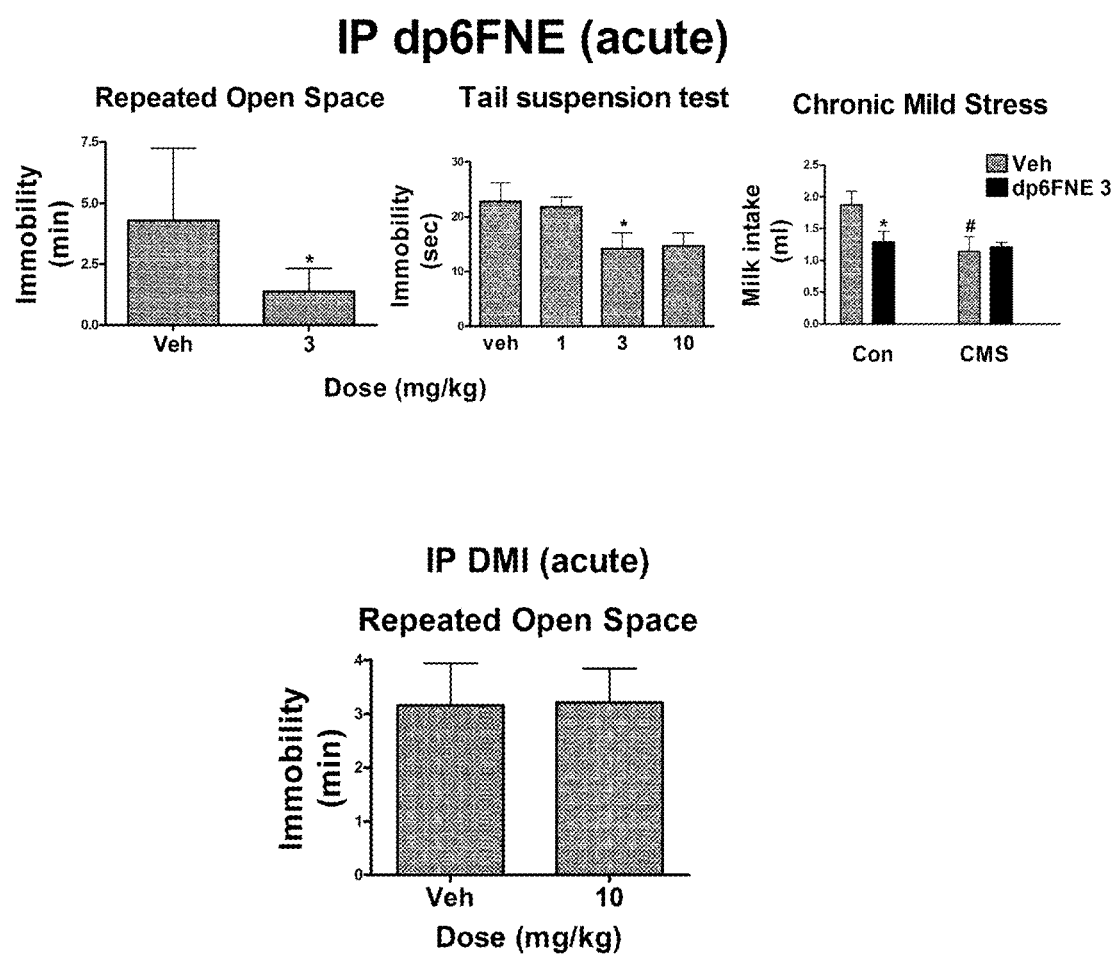
FIG. 14 Upper: demonstrates the effect of acute dp6FNE injected i.p. on open space swim, tail suspension and chronic mild stress depression tests. Lower: demonstrates the results of an acute DMI on open space test. Note complete lack of effect of acute DMI but strong effect of acute dp6FNE above in this test *p<0.1 vs Veh, #<0.05 vs Con. N=4-9/gp. *p≤0.05 versus vehicle, planned contrast.

The new compound, 6dpFNE, has significant antidepressant action in the repeated open-space swim and tail suspension tests following i.p. administration at doses of 1, 3 and 10 mg/kg (FIG. 14). In addition, an initial comparison of the speed of action of i.p. dp6FNE with that of i.p. administration of the tricyclic antidepressant, desipramine (DMI) was performed, in the repeated open-space swim model, which does not respond to acute treatment. Evidence demonstrates that the new drug has a significantly faster onset of action than the latter tricyclic (FIG. 14). A test of the effect of the new drug in the chronic mild stress (CMS)-anhedonia model using the consumption of sweetened milk as the hedonic measure was performed, and evidence demonstrates that dp6FNE eliminates the CMS reduction of intake but also induces significant hypophagia (FIG. 14). (The latter property may actually be beneficial as it would counter the weight gain frequently reported with antidepressant treatment (Richelson, *Mayo Clin Proc* 2001; 76: 511-527).) A subsequent test using a non-nutritive rewarding behavior, sniffing of estrous urine by male mice, discussed earlier, has shown that dp6FNE immediately overcomes the impairment of sniffing caused by previous administration of endotoxin.

The catecholamine pro-drug, dipivalyl-6-fluoronorepinephrine (dp6FNE) may be used in combination with the peripherally-acting α-adrenergic blocking agent, phentolamine, prazosin or cardevilol, for the rapid treatment of depression. It is commonly known that all currently available antidepressant drugs require several weeks administration to achieve their therapeutic effects (Sartorius, et al., *Int J Neuropsychopharmacol* 2007; 10 Suppl 1: S1-207). dp6FNE is a brain permeable pro-drug that is taken up centrally and enzymatically cleaved to form the active parent catecholamine, 6FNE, in all tissues including the brain. As discussed above, 6FNE, when administered in the brain via the 4th cerebral ventricle of the mouse, has immediate antidepressant activity in 4 independent screens (Stone, et al., *International Journal of Neuropsychopharmacology* (2010) In press)—the forced swim (Porsolt, et al., *Arch int Pharmacodyn Ther* 1977; 229: 327-336), tail suspension (Steru, et al., *Psychopharmacology* 1985; 85: 367-370), repeated open-space forced swim (Sun, et al., *J Neurosci Methods* 2003; 126: 35-40) and lipopolysaccharide-induced anhedonia test (Frenois, et al., *Psycho-*

*neuroendocrinology* 2007; 32: 516-531. In addition, data shows significant antidepressant activity of its systemically (i.p.) administered pro-drug (dp6FNE) in the tail suspension test, repeated open-space forced swim test and chronic mild stress-anhedonia models (FIG. 14).

Dp6FNE may be used for the immediate control of stress and anxiety. Intraventricular 6FNE inhibits the neural activity of two recognized major stress nuclei in the brain (the locus coeruleus (Valentino, et al., *Eur J Pharmacol* 2008; 583: 194-203) and paraventricular nucleus of the hypothalamus (Muigg, et al. *Biol Psychiatry* 2007; 61: 782-796)) during various stressful conditions and also reduces anxiety in the open field test (Defries, et al., *Behav Biol* 1974; 11: 481-495) as evidenced by a greater willingness to explore the center and risky areas of the field (Stone, et al., *International Journal of Neuropsychopharmacology* (2010) In press). Intracerebral administration of 6FNE also reduces behavioral inhibition in mice in their home cages resulting from handling and injection procedures which are stressful for mice (Stone, et al. *Brain Res* 2009; 1291: 21-31). In addition the pro-drug, will be tested for anxioltic effects in other tests of anxiety and stress such as the plus-maze (Pellow, et al., *J Neurosci Methods* 1985; 14: 149-167).

dp6FNE is unique in that the parent catecholamine, 6FNE, is the only known selective α-agonist that has full efficacy at all brain α-adrenoceptors (Johnson, et al. *Eur J Pharmacol* 1986; 129: 293-305; Johnson; et at, *Mol Pharmacol* 1987; 31: 239-246). All other $\alpha_1$-agonists, catecholamines or antidepressants that act on depression are either partial agonists (such as phenylephrine (Johnson, et al. *Eur J Pharmacol* 1986; 129: 293-305; Johnson; et al., *Mol Pharmacol* 1987; 31: 239-246; Law-Tho, et at, *Eur J Neurosci* 1993; 5: 1494-1500) and cirazoline (Thonberg; et al., *Biochemical Journal* 2002; 364: 73-79)), or are direct (norepinephrine and epinephrine) or indirect agonists (tricyclic antidepressants) at β-adrenergic receptors which can exacerbate depression and anxiety (Cole, et al., *J Pharmacol exp Ther* 1988; 247: 902-910; Kitada, et al., *Jpn J Pharmacol* 1983; 33: 867-873; Sulser, In: *Typical and Atypical Antidepressants: Molecular Mechanisms*, edited by Costa E and Racagni G. New York: Raven Press, 1982)), or are $\alpha_1$-receptor antagonists (tricyclic antidepressants (Richelson, Mayo *Clin Proc* 2001; 76: 511-527)).

6FNE is therefore a full agonist at both the $\alpha_1$- and $\alpha_2$-adrenoceptors which are colocalized in a key stress nucleus in the brainstem—the locus coeruleus—and which both inhibit the neural activity of this nucleus and hence of stress reactions. Although $\alpha_2$-adrenoceptors have long been known to inhibit the LC, $\alpha_1$-adrenoceptors have an even more profound inhibitory effect on this brain region, and that 6FNE is the most potent inhibitor yet found for this nucleus (Stone, et al. *Brain Res* 2009; 1291: 21-31). This has not been described in the literature previously. Thus the selectivity of this compound for α-adrenoceptors, its full agonist property and the fact that it stimulates both $\alpha_1$- and $\alpha_2$-adrenoceptors that are colocalized to the locus coeruleus give 6FNE greater therapeutic potential in both depression and anxiety than any other known catecholamine or compound yet developed. These properties of 6FNE probably account for the fact that it works significantly faster than other therapeutic agents.

dp6FNE may be used in combination with a peripheral α-receptor antagonist that does not enter the brain in order to prevent activation of peripheral α-adrenoceptors which may have opposing effects on depression and anxiety (Wong, et al., *Proc Natl Acad Sci USA* 2000; 97: 325-330; Yang, et al., *J Pharmacol exp Ther* 1990; 255: 1064-1070) or produce unwanted cardiovascular effects. Prazosin, an $\alpha_1$-adrenoceptor antagonist, which is not taken up by the brain (Stone, et al., *Eur. J. Pharmacol.* (2001) 420, 97-102), may also be used to block the peripheral actions of dp6FNE.

6FNE May be Better than a Pure $\alpha_2$-Agonist for Treatment of Depression.

It is known that intracerebral injection of the $\alpha_2$-adrenergic agonist, clonidine, can produce rapid antidepressant effects in rats in the forced swim or the stress-potentiated forced swim test (Simson, et al., *Neuropharmacology* 1986; 25: 385-389; Weiss, et al., *Neuropharmacology* 1986; 25: 367-384). Thus there is existing preclinical evidence that $\alpha_2$-agonists can produce antidepressant effects although these compounds are not routinely used for the treatment of human depression. Using 6FNE, that is derived from dp6FNE as the active agent, may provide advantages over simply using an $\alpha_2$-agonist alone to treat the disorder.

However, since 6FNE stimulates both the $\alpha_1$- and $\alpha_2$-adrenoceptors, it should have an advantage over using $\alpha_2$-agonists alone for depression. To further clarify this question the applicants carried out an experiment comparing intracerebral 6FNE with intracerebral administration of a highly selective full $\alpha_2$-agonist, dexmedetomidine, in mice on two tests for antidepressant activity, the tail suspension test and the repeated open-space forced swim test. The first test involves an acute stress-induced model of depression (Steru, et al., *Psychopharmacology* 1985; 85: 367-370) whereas the second, a more prolonged, chronic depression that is more akin to chronic human depression (Stone, et al., *Pharmacol Biochem Behav* 2008; 91: 190-195). Both 6FNE and dexmedetomidine were equally effective on the tail suspension test but only 6FNE was effective on the repeated open-space forced swim 6FNE therefore has the advantage over $\alpha_2$-agonists in that it is active on more types of depression and on an animal depression that is more similar to human depression.

Another advantage of using 6FNE over $\alpha_2$-agonists is that it has no sedative effect at higher doses. Sedation has not been observed, only behavioral activation, in a wide range of behavioral tests with intracerebral 6FNE (Stone, et al. *Brain Res* 2009; 1291: 21-31) or with peripheral administration of dp6FNE whereas α2-agonists produce strong soporific actions and can be used to supplement anesthesia (Hall, et al., *Brit J Anaesth* 2001; 86: 5-11), although a slight sedative effect was observed at low dosages (0.1-0.3 mg/kg) (Stone, Lin Y, Sarfraz Y, and Quartermain D, 2011) Sedation interferes with behavioral performance and is therefore a detrimental side effect to the treatment of major depressive illness in humans.

6FNE May be Better at Treating Depression than Other $\alpha_1$-Agonists.

There are reports that other $\alpha_1$-agonists can also reverse depression in rodents. It has been shown previously that direct intracerebal infusion of the partial $\alpha_1$-agonist, phenylephrine (PE), produced antidepressant effects in the forced swim test in rats (Kitada, et al., *Neuropharmacology* 1983; 22: 1055-1060) and that systemic administration of PE also had an anti-immobility effect in this test but only at a near lethal dose (16 mg/kg, i.p.) It has also recently been reported that another partial α1-agonist, cirazoline, when given chronically to mice in the drinking water had significant antidepressant effects in the forced swim test (Doze, et al., *Brain Res* 2009; 1285: 148-157) and also stimulated neurogenesis in the cerebral ventricle walls (Gupta, et al., *Mol Pharmacol* 2009; 76: 314-326), a frequent concomitant of successful antidepressant action (Koo, et al. *Neurosci Lett* 2009; 456: 39-43).

6FNE has a more rapid and/or greater antidepressant effect than either of these agonists because 6FNE is the only known selective α-agonist that has full efficacy at all brain α-adrenoceptors and 6FNE works within minutes (Stone, et al. 2011) whereas cirazoline was given to mice over several months prior to testing in one model (forced swim test) in the above experiment by Doze et al, 2009. The partial agonist PE, given intraventricularly, does not produce the same reversal of behavioral inhibition in the home cage after handling stress that 6FNE does (Stone, et al. *Brain Res* 2009; 1291: 21-31).

The partial agonist, cirazoline, which enters the brain after i.p. injection, was incapable of reversing behavioral inhibition in the home cage after handling stress and by itself resulted in a pronounced inhibition of movement and motor behavior. (Stone, E A, Lin Y, Quartermain, D, Unpublished results)

6FNE May be Better than Other $\alpha_1$- and $\alpha_2$-Agonists or Other Anxiolytics for the Treatment of Stress and Anxiety.

The Evidence that 6FNE has Anti-Stress/Anti-Anxiety Properties Consists of Findings that intraventricular 6FNE markedly suppresses neural activity in two key stress brain nuclei, the locus coeruleus and paraventricular nucleus of the hypothalamus (Stone, et al. *Brain Res* 2009; 1291: 21-31) during handling stress, open-space forced swimming and, to a lesser degree, tail suspension stress. The compound also overcomes the behavioral inhibitory effect of handling stress on exploratory behavior in both the home cage and the open field and rescues the ability of handling-stressed mice to enter the more risky center regions of the field.

It is known however that $\alpha_2$-agonists, such as clonidine, can be used in the treatment of anxiety (Coplan, et al., *Psychopharmacology Bulletin* 1997; 33: 193-204). Furthermore, it has also been found that the intracerebral infusion of the partial $\alpha_1$-agonist, PE, is capable of moderately activating exploration in the home cage in handled rats (Stone, et al., *Synapse* 2004; 54: 164-172) while other investigators have found that infusion of this drug in the hypothalamus can exert an anxiolytic effect (Talalaenko, et al., *Neuroscience & Behavioral Physiology* 2003; 33: 255-261) and that injection of high peripheral doses can counter anxiety in the plus-maze (Zarrindast, et al., *Eur J Pharmacol* 2000; 407: 145-158). Also, peripheral administration of the antidepressant, mirtazepine, counters freezing behavior, a manifestation of anxiety in rats, and this effect appears to be mediated by $\alpha_1$-adrenoceptors. However, some have shown that intracerebral infusion of $\alpha_1$-agonists in the prefrontal cortex can produce behavioral disruption similar to anxiety (Arnsten, et al., *Biol Psychiatry* 1999; 45: 26-31).

The present data, however, indicate that intracerebal 6FNE or peripheral dp6FNE has greater anti-stress and anti-anxiety effects than clonidine or PE, given centrally or peripherally, and more rapid effects than mirtazepine for the following reasons:

Ivt. 6FNE immediately inhibits neural activity in the locus coeruleus and does so much more potently than a full $\alpha_2$-agonist, dexmedetomidine, that is more selective than clonidine (Stone, et al. *Brain Res* 2009; 1291: 21-31; Takano, et al., *J Pharmacol exp Ther* 1991; 258: 438-446). Furthermore, 6FNE rescues exploratory behavior in the home cage of handling-stressed mice to a much greater extent than does either dexmedetomidine, PE or combined dexmedetomidine and PE (Stone et al., ibid).

Figure 15:
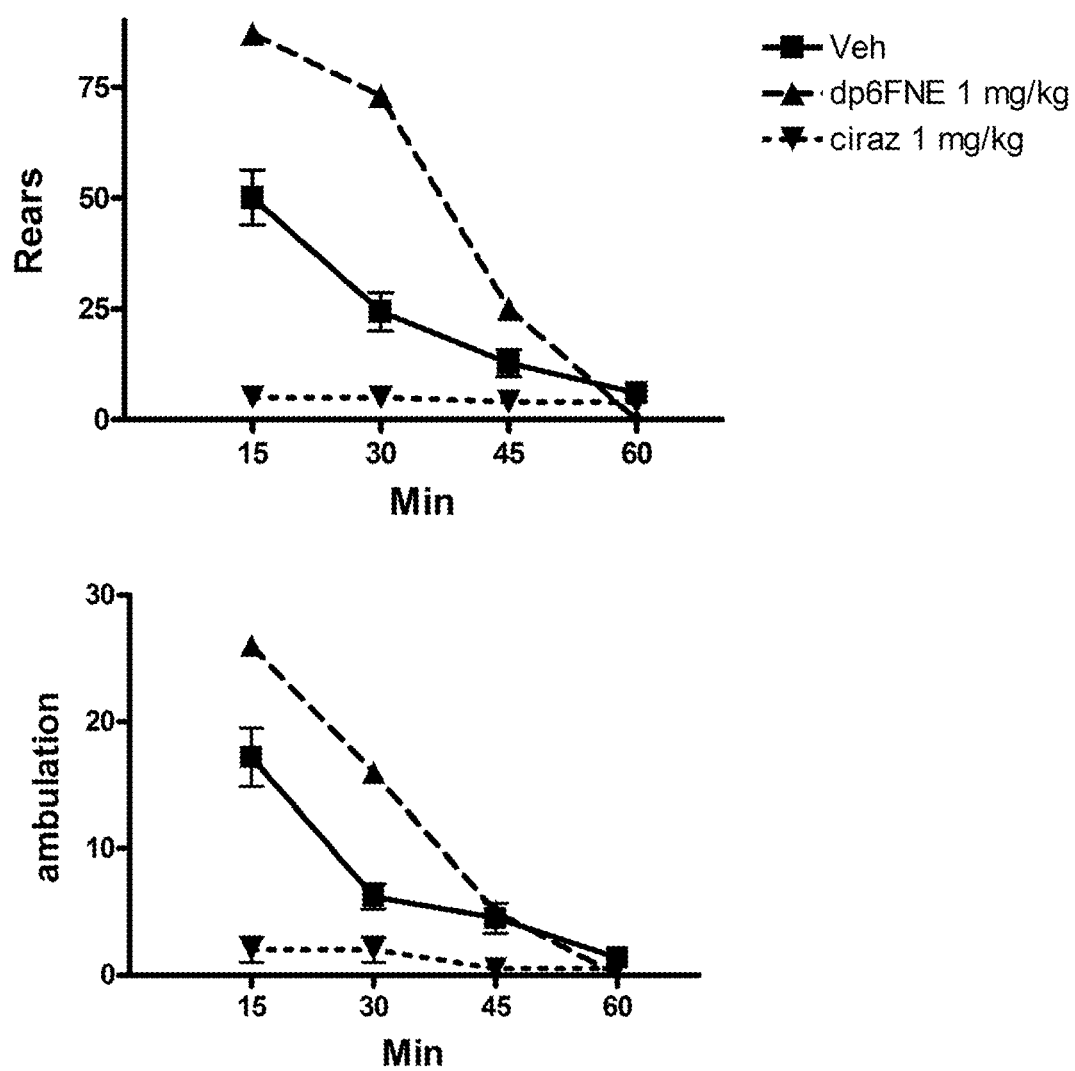
FIG. 15 depicts the effect of acute i.p. dp6FNE (1 mg/kg) or cirazoline (0.1 mg/kg), (N=1), on home cage activity in terms of rearing and ambulation, Veh (N=12).

The same rescue of home cage exploration in handling-stressed mice given i.p. injections of dp6FNE in the presence of phentolamine was observed (FIG. 15). It is known that peripheral administration of $\alpha_1$-agonists without phentolamine impairs exploratory behavior in the open field (Yang, et al., *J Pharmacol exp Ther* 1990; 255: 1064-1070). Furthermore the partial $\alpha_1$-agonist, cirazoline, failed to affect anxiety as measured by behavioral inhibition in the light/dark box test or the elevated plus-maze test in mice even after months of chronic treatment (Doze, et al., *Brain Res* 2009; 1285: 148-157). In addition, as noted above, cirazoline is not effective in reducing behavioral inhibition in the home cage following handling and injection stress (FIG. 12).

An additional advantage of 6FNE (or dp6FNE with prazosin or phentolamine) over clonidine and other anxiolytics such as the benzodiazepines for the treatment of stress and/or anxiety, is that it is non-sedative and produces no obvious CNS impairment at doses above 1 mg/kg, i.p. Thus this agent can produce equivalent anti-anxiety effects to these traditional anxiolytics without their sedative and impairing effects.

dp6FNE Plus Prazosin or Phentolamine May be Better than any Other Peripheral Catecholamine Treatment for Either Depression or Stress/Anxiety.

Although catecholamines have long been implicated in the treatment of depression, it has not been possible previously to produce an antidepressant response by administering a catecholamine systemically. Systemic catecholamines generally produce increases in anxiety (Yang, et at, *J Pharmacol exp Ther* 1990; 255: 1064-1070) and depression (Wong, et al., *Proc Natl Acad Sci USA* 2000; 97: 325-330; Metzer, et al., *Headache* 1987; 27: 571-572). dp6FNE plus prazosin or phentolamine is therefore the first and only existing peripheral catecholamine preparation that works therapeutically in these conditions. Moreover, it is either significantly more rapid (i.e., versus other antidepressants) or more effective (i.e., versus other $\alpha_1$- and $\alpha_2$-agonists) than other treatments. Neither of these properties could be predicted from what was known prior to our researches with this compound.

6FNE is not Another Catecholamine Stimulant

6FNE and dp6FNe were tested for their effects on motor activity by measuring locomotor behavior in an open field after either ivt. (6FNE) or i.p. injection (dp6fNE) in mice. These mice were compared to animals that were either non handled or received either a vehicle ivt injection or an i.p. injection of the stimulant, amphetamine (5 mg/kg). The results are shown in FIG. 6 and in (Stone, Lin Y, Sarfraz Y, and Quartermain D, 2011). 6FNE produced no change in activity compared to the non-handled animals but did produce a small increase compared to the vehicle injected mice. Furthermore, the increase in activity after 6FNE was minor in comparison with the bona fide stimulant, amphetamine which produced a 10 fold increase. The small increase over the vehicle group therefore appears to be the result of a reduction of the stress caused by the handling and restraint for the ivt. injection which is in agreement with the reduced activation of brain stress circuits discussed above. This interpretation was supported by an examination of the time in the center or risky area of the field spent by the various groups. Vehicle injection significantly reduced the time in the center whereas 6FNE restored this behavior back to the level of the non-handled controls. Dp6FNE did not produce any stimulation of motor behavior and also produced a significant increase in the time in the center of the field. A slight reduction in motor behavior at the low doses (0.1-0.3 mg/kg) were, however, observed.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

What is claimed is:

1. A pharmaceutical composition to treat an anxiety disorder or a mood disorder comprising a cocktail of at least two inhibitors of central stress nuclei, wherein at least one inhibitor of the central stress nuclei is a compound according to formula IIIa, IIIb, or IIIc:

IIIa

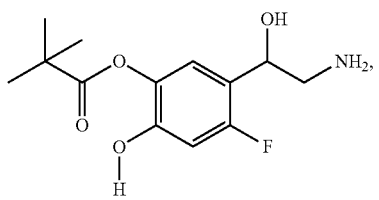

IIIb

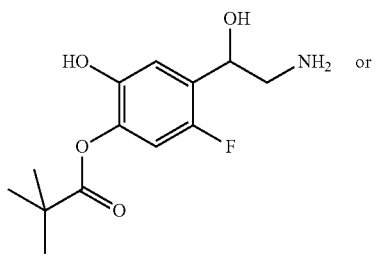 or

IIIc

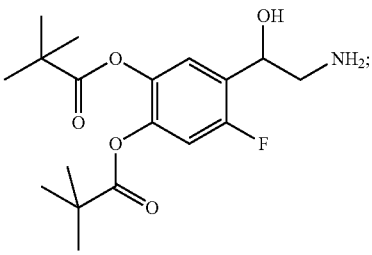

or a pharmaceutically acceptable salt, or solvate thereof; and stereoisomers, isotopic variants and tautomers thereof.

2. A method for treating α-adrenergic mediated disease or condition in a mammal comprising the step of administering to said mammal a pharmaceutical composition according to claim 1.

3. The method according to claim 2, wherein the disease or condition is an anxiety disorder, a mood disorder or imminent suicidal behavior.

* * * * *